United States Patent
Post et al.

(10) Patent No.: US 12,275,916 B2
(45) Date of Patent: Apr. 15, 2025

(54) ODORANT SECONDARY ALCOHOLS AND THEIR COMPOSITIONS

(71) Applicant: S H KELKAR & COMPANY LIMITED, Mumbai (IN)

(72) Inventors: Freddy Post, Arnhem (NL); Leszek Doszczak, Amersfoort (NL); Nitesh Chaudhari, Mumbai (IN); Raju Kapse, Mumbai (IN)

(73) Assignee: S H KELKAR & COMPANY LIMITED, Mumbai (IN)

( * ) Notice: Subject to any disclaimer, the term of this patent is extended or adjusted under 35 U.S.C. 154(b) by 1143 days.

(21) Appl. No.: 17/250,115

(22) PCT Filed: May 23, 2019

(86) PCT No.: PCT/EP2019/063358
§ 371 (c)(1),
(2) Date: Nov. 30, 2020

(87) PCT Pub. No.: WO2019/228903
PCT Pub. Date: Dec. 5, 2019

(65) Prior Publication Data
US 2021/0284929 A1  Sep. 16, 2021

(30) Foreign Application Priority Data

May 31, 2018 (IN) .............................. 201821020411
Jul. 25, 2018 (EP) ..................................... 18185509

(51) Int. Cl.
| | | |
|---|---|---|
| C11D 3/50 | (2006.01) | |
| A23L 27/20 | (2016.01) | |
| A61K 8/34 | (2006.01) | |
| A61Q 5/02 | (2006.01) | |
| C07C 29/143 | (2006.01) | |
| C07C 31/125 | (2006.01) | |
| C07C 33/025 | (2006.01) | |
| C11B 9/00 | (2006.01) | |

(52) U.S. Cl.
CPC ........ *C11B 9/0015* (2013.01); *A23L 27/2026* (2016.08); *A61K 8/34* (2013.01); *A61K 8/342* (2013.01); *A61Q 5/02* (2013.01); *C07C 29/143* (2013.01); *C07C 31/125* (2013.01); *C07C 33/025* (2013.01); *A23V 2002/00* (2013.01)

(58) Field of Classification Search
CPC ....... C11D 3/50; C11B 9/0015; C07C 29/143; C07C 31/125; C07C 33/025; A61Q 5/02; A61K 8/34; A61K 8/342; A23L 27/2026
See application file for complete search history.

(56) References Cited

U.S. PATENT DOCUMENTS

| | | |
|---|---|---|
| 4,405,820 A | 9/1983 | Boden |
| 5,756,821 A | 5/1998 | Erich et al. |

OTHER PUBLICATIONS

Snider et al, "Dimethylaluminum Chloride Catalyzed Ene Reactions of Aldehydes", Journal of the American Chemical Society, American Chemical Society, US, vol. 104, No. 2, pp. 555-563, Jan. 1, 1982.*
International Search Report and Written Opinion mailed Sep. 30, 2019 in related PCT Application No. PCT/EP2019/063358.
Haller et al., "Methylation de l'isovalérone au moyen de l'amidure de sodium et de l'iodure de méthyle. Tétraméthylisovalérone ou hexaméthyd-2.3.3.5.5.6-heptanone-4", Apr. 28, 1913 (Apr. 28, 1913), vol. 156, No. 1, p. 1295-1298.
Barbot et al., "Action d'organométalliques ?-éthyléniques sur les esters; applications de l'isomérisation thermique d'alcoolates zinciques à la préparation d'alcools ?, ?'-diethyléniques", Bulletin De La Societe Chimique De France, Societe Francaise De Chimie. Paris, France,No. 6, Jan. 1, 1989 (Jan. 1, 1989), p. 864-871.
Suzuki et al., "Transition-Metal-Free Reductive Coupling of 1,3-Butadienes with Aldehydes Catalyzed by Dibutyliodotin Hydride", Organic Letters,vol. 19, No. 19, Oct. 6, 2017 (Oct. 6, 2017), p. 5392-5394.
Snider et al., "Dimethylaluminum Chloride Catalyzed Ene Reactions of Aldehydes", Journal of the American Chemical Society, American Chemical Society, US, vol. 104, No. 2, Jan. 1, 1982 (Jan. 1, 1982), p. 555-563.
Smith et al., "3-Chloro-1-lithiopropene, a Functional Organolithium Reagent, and Its Reactions with Alkylboronates To Give 3-Alkylprop-1-en-3-ols", Journal of Organic Chemistry, vol. 78, No. 18, Sep. 2013 (Sep. 2013), p. 9526-9531.
Ramos et al., "Functionalisation of terpenoids at C-4 via organopalladium dimers: cyclopropane formation during oxidation of homoallylic @s-organopalladium intermediates with lead tetraacetate", Tetrahedron, Elsevier Science Publishers, Amsterdam, NL, vol. 63, No. 51, Nov. 8, 2007 (Nov. 8, 2007), p. 12608-12615.
Dubois et al., "Friedel-Crafts Acylation of Substituted Olefins—Synthesis of Hindered Unsaturated-Ketones", Bulletin De La Societe Chimique De France, Societe Francaise De Chimie. Paris, France, No. 3-4, Jan. 1, 1984 (Jan. 1, 1984), p. 133-138.
Pierre et al., "The sec-butyl cation; reaction with 2-butene", Canadian Journal of Chemistry, vol. 59, No. 17, 1981, p. 2621-2628.
Herr et al., "The Wolff-Kishner Reaction at Atmospheric Pressure", Journal of the American Chemical Society, vol. 67, 1945, p. 2061-2063.
Invitation to pay additional fees mailed Jun. 24, 2019 in related PCT Application No. PCT/EP2019/063358.

* cited by examiner

*Primary Examiner* — Brian P Mruk
(74) *Attorney, Agent, or Firm* — MASCHOFF BRENNAN

(57) ABSTRACT

The present invention relates to new classes of odorous alcohols (odorants) derived from 2,3-dimethylbutene which are useful as fragrance or flavor materials in particular in providing natural piney olfactory notes with a complex profile to perfume, aroma or deodorizing/masking compositions.

20 Claims, No Drawings

ODORANT SECONDARY ALCOHOLS AND THEIR COMPOSITIONS

FIELD OF THE INVENTION

The present invention relates to a new class of odorous alcohols which are useful as fragrance or flavor materials in particular in providing natural piney olfactory notes with a complex odorous profile to perfume, aroma or deodorizing/masking compositions and also conferring to said compositions one or more of the following advantages/properties: cooling-effect properties similar to menthol but with a more natural impression, high diffusivity, and/or solubility. The present invention also relates to fragrance, flavor and/or deodorizing/masking compositions comprising said new classes of odorant alcohols. The present invention furthermore refers to the said odorants which can be used in the novel fragrance, flavor and/or deodorizing/masking compositions of the present invention. The present invention also refers to a method for the production of the said odorants/compounds and of the corresponding fragrance, flavor and/or deodorizing/masking compositions containing said odorants/compounds.

BACKGROUND OF THE INVENTION

Perfumery industry and/or the flavor industry mainly utilize synthetic molecules as raw ingredients. Especially, the introduction of novel odorants/compounds and/or for novel fragrance, flavor and/or deodorizing/masking compositions comprising said odorants/compounds is desirable.

For industrial applications it is beneficial when various products can be derived from one basic scaffold/raw material. It becomes even more beneficial if the raw material is exclusive in certain aspects. 2,3-Dimethylbutenes (1) and (2) are almost exclusively used for production of substituted tetralines (3) and in particular in production of Tonalid (4).

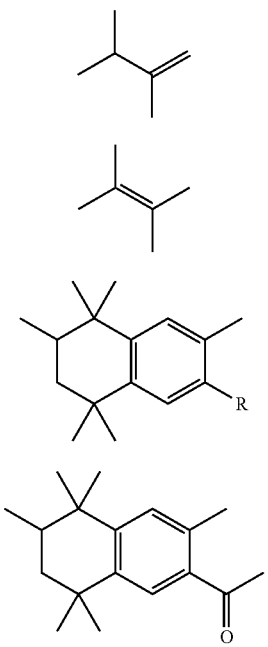

Therefore, in the course of their research and development activities, the Applicants started to develop products based on 2,3-dimethylbutenes (1) and (2) as a raw material(s) for novel odorants. It is an advantage of one or more of the embodiments of the present invention that the claimed odorants/compounds derived from 2,3-dimethybutenes can impart and/or accentuate particular olfactory notes, in particular providing natural piney olfactory notes with a complex odorous profile to fragrance, flavor and/or deodorizing/masking compositions, and also confer to said compositions one or more of the following advantages/properties: cooling-effect properties similar to menthol but with a more natural impression, high diffusivity, and/or solubility.

The article by Haller and Bauer entitled «Methylation of isovalerone» (Comptes rendus hebdomadaires des séances de l'Académie des sciences, vol. 156, no. 1, 28 Apr. 1913, pages 1295-1298) discloses methods for methylation of isovalerone. On pages 1297-1298, the authors describe the synthesis of 2,3,3,5,5,6-hexamethylheptan-4-one (tetramethylisovalerone). Since the newly synthesized tetramethylisovalerone did not form oximes nor semicarbazones (in other words, the compound did not undergo characteristic reactions for qualitative analysis of carbonyl compounds used in the days before spectroscopic methods were available) the authors decided to reduce the putative ketone to an alcohol which by reacting with phenyl isocyanate should form a respective phenyluretane thus proving the successful synthesis of the desired tetramethylisovalerone. The intermediate alcohol synthesized for analytical purposes (2,3,3,5,5,6-hexamethylheptan-4-ol), exhibited a strong borneol-like odor.

The article from Barbot et al. entitled "Action d'organometalliques alpha-ethyleniques sur les esters; applications de l'isomerisation thermique d'alcoolates zinciques a la preparation d'alcools beta, beta'-diethyleniques» (Bulletin de la Societe Chimique de France, Societe Francaise de Chimie. Paris, France, n6, 1 Jan. 1989, pages 864-871), respectively discloses 2,3,3,5,5,6-hexamethylhepta-1,6-dien-4-ol and 2,3,3,6,7-pentamethylocta-1,6-dien-4-ol obtained by double addition of Grignard reagents to methyl formate.

The article by Suzuki et al. entitled «Transition-Metal-Free Reductive Coupling of 1,3-Butadienes with Aldehydes Catalyzed by Dibutyliodotin Hydride» (Organic Letters, vol. 19, n$_o$. 0.19, 6 Oct. 2017, pages 5392-5394), discloses 2,4,4,5-tetramethylhex-5-en-3-ol and 2,3,3,6-tetramethyl-hept-1-en-4-ol in the context of their studies on the coupling of 1,3-dienes with aldehydes in order to realise coupling reactions without the use of transition-metal catalysts.

The article by Snider et al. entitled «Dimethylaluminum chloride catalyzed ene reactions of aldehydes», (J. Am. Chem. Soc., 1982, 104 (2), pp 555-563), discloses 3,3,4-trimethylpent-4-en-2-ol and 2,3,3,6-tetramethylhept-1-en-4-ol obtained via an ene reactions of aliphatic and aromatic aldehydes mediated by dimethylaluminum chloride. The article by Smith et al. discloses "3-Chloro-1-lithiopropene, a Functional Organolithium Reagent, and Its Reactions with Alkylboronates To Give 3-Alkylprop-1-en-3-ols", J. Org. Chem., 2013, 78 (18), pp 9526-9531 discloses 4,4,5-trimethylhex-1-en-3-ol.

SUMMARY OF THE INVENTION

This invention discloses novel fragrance, flavor and/or deodorizing/masking compositions comprising an alcohol selected from compounds of formula (7) or of formula (8)

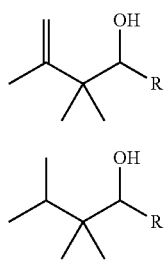

wherein R is an alkyl group having from 1 to 6 carbon atoms or an alkenyl group having from 2 to 6 carbon atoms, and wherein compound of formula (8) can't be 2,3,3,5,5,6-hexamethylheptan-4-ol.

In an embodiment according to the present invention, R is methyl, ethyl, n-propyl, i-propyl, n-butyl, s-butyl, t-butyl, i-butyl, 2-methylprop-1-en-2-yl, n-pentyl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

In another embodiment the compounds of this invention can be chiral, e.g. they can occur as stereoisomeric mixtures, more specifically as mixture of enantiomers; R isomer, S isomer, a racemic mixture and/or a non-racemic mixture of R and S isomers and they can also be advantageously used in pure form or as mixtures.

In another embodiment the compounds of this invention in which the R group is an alkenyl can occur as isomeric mixtures, more specifically as Z isomer, E isomer, and/or a mixture of Z and E isomers and they can also be advantageously used in pure form or as mixtures.

DETAILED DESCRIPTION

The term "odorant" characterizing the compounds according to the present invention means that in humans it triggers an odor sensation which is preferably pleasant; it is therefore conventionally used for perfuming industrial and sanitary articles, washing agents, cleaning agents, personal hygiene products, cosmetics and the like. For the purposes of the present invention and appended claims, the term "odorant" includes "aroma substances". Aroma substances is the term usually used to designate substances which provide odor and/or flavor to foodstuffs.

The alcohol compounds of formula (7) or of formula (8) may be used alone, as mixtures thereof, or in combination with a base material.

As used herein, the "base material" includes all known fragrance/flavor materials selected from the extensive range of natural products like: essential oils, extracts, resinoids or isolates and synthetic materials, such as: hydrocarbons, alcohols, aldehydes and ketones, ethers and acetals, esters and lactones, nitriles, oximes or heterocycles, and/or in admixture with one or more ingredients or excipients/adjuvants conventionally used in conjunction with odorants in fragrance and/or flavor compositions, for example: solvents/diluents, stabilizers, carrier materials, and other auxiliary agents commonly used in the art.

The alcohol compounds according to formula (7) or to formula (8) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients.

According to a preferred embodiment of the invention, the fragrance, flavor and/or deodorizing/masking composition according to the present invention contains at least one alcohol compound according to formula (7) or formula (8) as previously described, in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the compound of formula (7) or of formula (8) according to the present invention, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

The compounds of formula (7) or of formula (8) as described hereinabove may be employed in a consumer product base simply by directly mixing at least one compound of formula (7) or of formula (8), or a fragrance composition comprising said compound of formula (7) or of formula (8) with the consumer product base; or they may, in an earlier step, be entrapped with an entrapment material, for example, polymers, capsules, microcapsules and/or nanocapsules, liposomes, film formers, absorbents such as active carbon or zeolites, cyclic oligosaccharides, cyclic glycourils, and mixtures of two or more thereof, or they may be chemically bonded to substrates, which are adapted to release the fragrance molecule upon application of an external stimulus such as light, enzyme, air, water or the like, and then mixed with the consumer product base.

Thus, the invention can be useful for existing methods of manufacturing a fragrance, flavor and/or deodorizing/masking composition, comprising the incorporation of a compound of formula (7) or of formula (8), as a fragrance, flavor and/or deodorizing/making ingredient, either by directly admixing the compound to the consumer product base or by admixing a fragrance, flavor and/or deodorizing/masking composition comprising said compound of formula (7) or of formula (8), which may then be mixed with a consumer product base, using conventional techniques and methods. Through the addition of an olfactory-acceptable amount of at least one compound of formula (7) or of formula (8) of the present invention as hereinabove described, the odor notes of a consumer product base can be improved, enhanced, and/or modified.

The present invention provides fragrance, flavor and/or deodorizing/masking compositions comprising an alcohol selected from compounds of formula (7) or of formula (8)

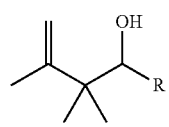

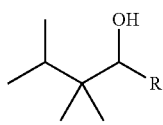

(8)

wherein R is an alkyl group having from 1 to 6 carbon atoms or an alkenyl group having from 2 to 6 carbon atoms, and wherein compound of formula (8) can't be 2,3,3,5,5,6-hexamethylheptan-4-ol.

In an embodiment according to the present invention, R is methyl, ethyl, n-propyl, i-propyl, n-butyl, s-butyl, t-butyl, i-butyl, 2-methylprop-1-en-2-yl, n-pentyl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

In an embodiment according to the present invention
for the compounds of formula (7) R can't be methyl, i-propyl, or i-butyl, and
for the compounds of formula (8) R can't be methyl, i-propyl, or vinyl.

In an embodiment according to the present invention, R can't be methyl, i-propyl, i-butyl or vinyl.

In an embodiment according to the present invention, the compound of formula 7 can't be 2,3,3,5,5,6-hexamethyl-hepta-1,6-dien-4-1 or 2,3,3,6,7-pentamethylocta-1,6-dien-4-ol.

In an embodiment according to the present invention, the fragrance, flavor and/or deodorizing/masking composition comprises the compound of formula (7) or of formula (8) which is selected from any of the compounds named or drawn in the following table

| Structure | Chemical name |
| --- | --- |
|  | 4,4,5-trimethylhex-5-en-3-ol |
|  | 4,4,5-trimethylhexan-3-ol |
|  | 3,3,4-trimethylpent-4-en-2-ol |
|  | 3,3,4-trimethylpentan-2-ol |
| 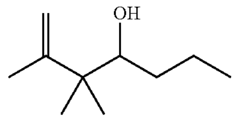 | 2,3,3-trimethylhept-1-en-4-ol |
| 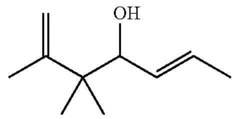 | 2,3,3-trimethylhepta-1,5-dien-4-ol |
| 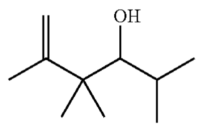 | 2,4,4,5-tetramethylhex-5-en-3-ol |
| 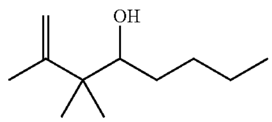 | 2,3,3-trimethyloct-1-en-4-ol |
| 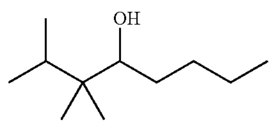 | 2,3,3-trimethyloctan-4-ol |
| 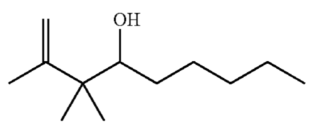 | 2,3,3-trimethylnon-1-en-4-ol |
| 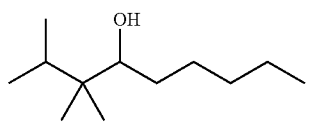 | 2,3,3-trimethylnonan-4-ol |
|  | 2,3,3,5-tetramethylhept-1-en-4-ol | and/or a mixture of two or more of the said compounds.

The Applicants have also discovered that, from an olfactory perspective, the compounds of formula (7) or of formula (8) have a distinctly natural piney profile that lends itself directly to use in herbal, aromatic and citrus compositions without a 'synthetic' effect. The compounds of formula (7) or of formula (8) provide sparkling freshness to the compositions and exhibit cooling-effect properties similar to menthol but with a more natural impression.

For example, when R is selected as ethyl in the compound (7), the Applicants have discovered that from an olactory perspective, the compound has a distinct natural quality reminding fir-needle and peppermint oil combined, together with a cooling sensation. Furthermore, compared to other odorants like e.g. borneol, this compound has greater diffusivity, adding even further to the natural effect.

Alcohols

In an embodiment, the present invention also provides new compounds of formula (7) useful in the perfume, aroma and/or deodorizing/masking compositions of the present invention

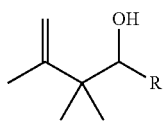

wherein R is an alkyl group having from 2 to 6 carbon atoms, or an alkenyl group having from 2 to 6 carbons, with the proviso that R can't be i-propyl, or i-butyl, and compound of formula 7 can't be 2,3,3,5,5,6-hexamethyl-hepta-1,6-dien-4-ol or 2,3,3,6,7-pentamethylocta-1,6-dien-4-ol.

In an embodiment according to the present invention which is applicable to compounds of formula (7), R is ethyl, n-propyl, n-butyl, s-butyl, t-butyl, 2-methylprop-1-en-2-yl, n-pentyl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

In another embodiment which is applicable to compounds of formula (7), R is a linear alkyl group having from 2 to 6 carbon atoms, or an alkenyl group having from 2 to 6 carbons.

In an embodiment, the present invention also provides new compounds of formula (8) useful in the perfume, aroma and/or deodorizing/masking compositions of the present invention

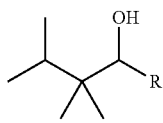

wherein R is an alkyl group having from 2 to 6 carbon atoms, or an alkenyl group having from 3 to 6 carbons, with the proviso that R can't be i-propyl and compound of formula (8) can't be 2,3,3,5,5,6-hexamethylheptan-4-ol.

In an embodiment according to the present invention, which is applicable to compounds of formula (8), R is ethyl, n-propyl, n-butyl, s-butyl, t-butyl, i-butyl, n-pentyl, 2-pentyl, 3-pentyl, n-hexyl, 2-hexyl, 3-hexyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

In another embodiment which is applicable to compounds of formula (8), R is a linear alkyl group having from 2 to 6 carbon atoms, or an alkenyl group having from 3 to 6 carbons.

In an embodiment according to the present invention, the new compounds of formula (7) and/or of formula (8) useful in the perfume, aroma and/or deodorizing/masking compositions of the present invention are selected from any of the compounds named or drawn in the following table

| Alcohol Structure | Chemical name |
|---|---|
| | 4,4,5-trimethylhex-5-en-3-ol |
| | 4,4,5-trimethylhexan-3-ol |
| | 2,3,3-trimethylhept-1-en-4-ol |
| | (E)-2,3,3-trimethylhepta-1,5-dien-4-ol |
| | 2,3,3-trimethyloct-1-en-4-ol |
| | 2,3,3-trimethyloctan-4-ol |
| | 2,3,3-trimethylnon-1-en-4-ol |
| | 2,3,3-trimethylnonan-4-ol |
| | 2,3,3,5-tetramethylhept-1-en-4-ol | and/or a mixture of two or more of the said compounds.

Preparation

In a preferred embodiment according to the present invention, the compounds of formula (7) and/or of formula (8) can advantageously be prepared from 2,3-dimethylbutene(s) via a sequence of acylation, optional hydrogenation and carbonyl reduction reactions sequence as illustrated hereafter.

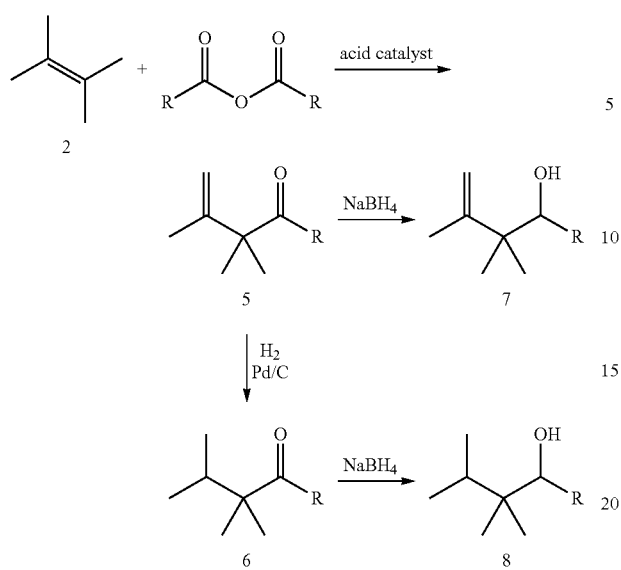

wherein R is an alkyl group having from 1 to 6 carbon atoms or an alkenyl group having from 2 to 6 carbon atoms.

In a preferred embodiment according to the present invention, the compounds of formula (7) and/or of formula (8) can advantageously be prepared from 2,3-dimethylbut-1-en via a sequence of acylation, optional hydrogenation and carbonyl reduction reactions sequence as illustrated hereafter.

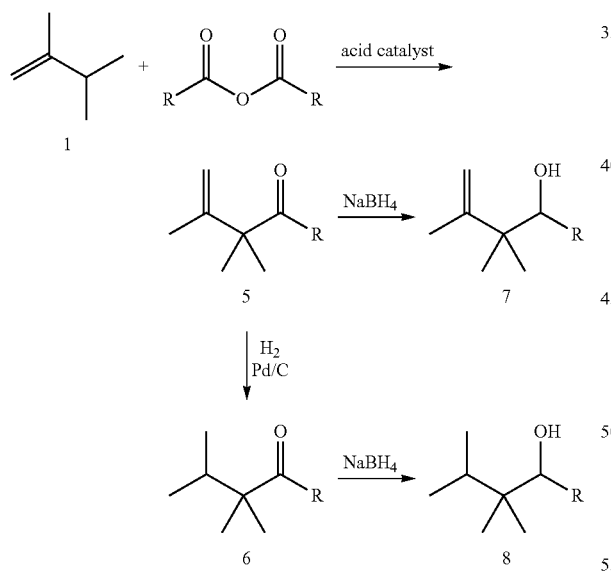

In an embodiment, the trimethyl alkenol of formula (7) and the trimethyl alkanol of formula (8) can advantageously be prepared from the corresponding ketones 5 or 6 respectively by reducing the carbonyl group of compounds of formula (5) or of formula (6). Any appropriate carbonyl reduction process can be used. In an embodiment according to the present invention, sodium borohydride in ethanol and water mixture is advantageously used.

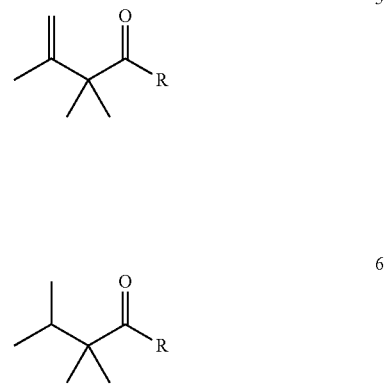

In another embodiment, the the trimethyl alkanol of formula (8) can advantageously be prepared from the corresponding ketone 5 by directly reducing both the carbonyl group and the double bond of compounds of formula 5. Any appropriate reduction process can be used. In an embodiment according to the present invention, hydrogen in presence of Pt/C can be advantageously used.

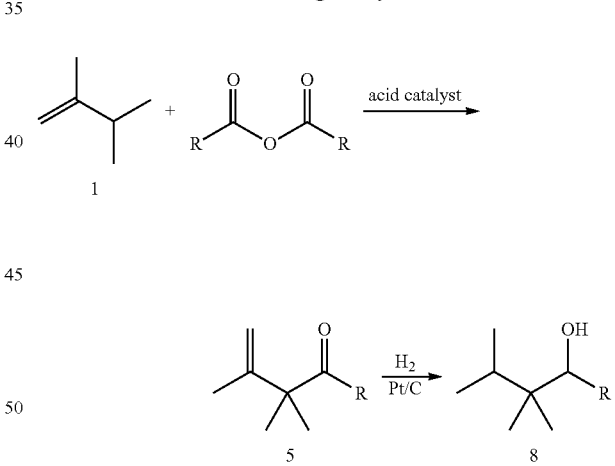

The table below illustrates the said corresponding ketones (identified as "parent" ketone in this description and appended claims) represented by general formula 5 or 6.

| Corresponding Ketones | Alcohol Structure | Chemical name |
|---|---|---|
| | | 4,4,5-trimethylhex-5-en-3-ol |

-continued

| Corresponding Ketones | Alcohol Structure | Chemical name |
|---|---|---|
| 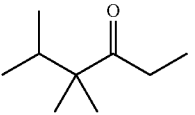<br>4,4,5-trimethylhexan-3-one | 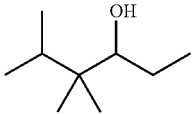 | 4,4,5-trimethylhexan-3-ol |
| 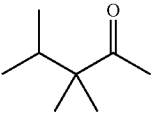<br>3,3,4-trimethylpentan-2-one | 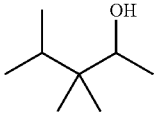 | 3,3,4-trimethylpentan-2-ol |
| 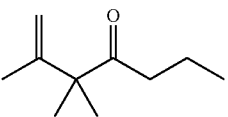<br>2,3,3-trimethylhept-1-en-4-one | 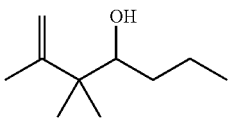 | 2,3,3-trimethylhept-1-en-4-ol |
| 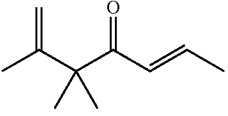<br>(E)-2,3,3-trimethylhepta-1,5-dien-4-one | 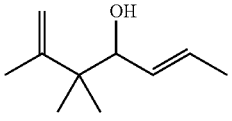 | (E)-2,3,3-trimethylhepta-1,5-dien-4-ol |
| 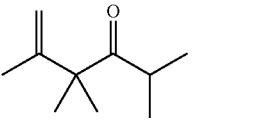<br>2,4,4,5-tetramethylhex-5-en-3-one | 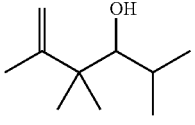 | 2,4,4,5-tetramethylhex-5-en-3-ol |
| 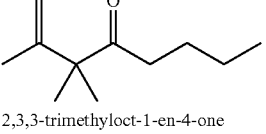<br>2,3,3-trimethyloct-1-en-4-one | 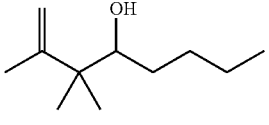 | 2,3,3-trimethyloct-1-en-4-ol |
| 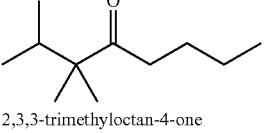<br>2,3,3-trimethyloctan-4-one | 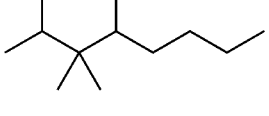 | 2,3,3-trimethyloctan-4-ol |
| 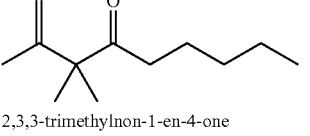<br>2,3,3-trimethylnon-1-en-4-one | 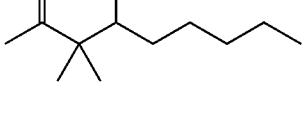 | 2,3,3-trimethylnon-1-en-4-ol |
| 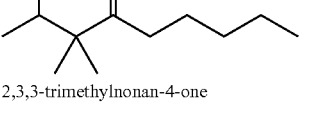<br>2,3,3-trimethylnonan-4-one | 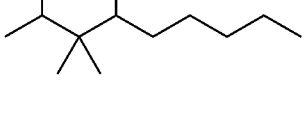 | 2,3,3-trimethylnonan-4-ol |
| 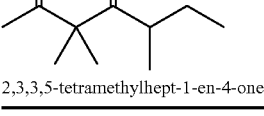<br>2,3,3,5-tetramethylhept-1-en-4-one | 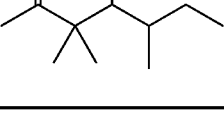 | 2,3,3,5-tetramethylhept-1-en-4-ol |

2,3-dimethylbutenes

The 2,3-dimethylbutenes compounds according to the present invention can be selected from 2,3-dimethyl-1-butene, 2,3-dimethyl-2-butene, or a mixture thereof; preferably from 2,3-dimethyl-2-butene or from a mixture of 2,3-dimethyl-2-butene and 2,3-dimethyl-1-butene.

Optional Isomerisation Step

In an embodiment according to the present invention, an isomerisation step is preferably performed in order to convert 2,3-dimethyl-1-butene into 2,3-dimethyl-2-butene. This isomerisation step is preferably performed for example when the starting material is 2,3-dimethyl-1-butene or when the starting material is a mixture of 2,3-dimethyl-2-butene and 2,3-dimethyl-1-butene having a content of 2,3-dimethyl-1-butene superior to the content of 2,3-dimethyl-2-butene. Any appropriate olefin isomerisation process can be used, as illustrative and non-restricting examples, base-catalysed and/or acid-catalysed isomerisation process can advantageously be used. In an embodiment according to the present invention, an ion-exchange resin acid catalyst, e.g. an Amberlyst catalyst in the acid form is advantageously used.

Acylation Synthesis Step

Thus, in an embodiment of the present invention, the 2,3-dimethylbutene(s) are subjected to an acylation synthesis step to form the ketones of formula (5) which can be represented by the following formula

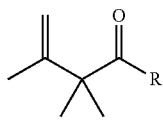

5 wherein R is an alkyl group having from 1 to 6 carbon atoms or an alkenyl group having from 2 to 6 carbon atoms.

In an embodiment of the present invention, the product is obtained by reacting 2,3-dimethylbutene(s) with acyl anhydride or acyl chloride, preferably followed by usual workup (e.g. aqueous wash, removal of unreacted reactants and/or solvents and distillation). In an embodiment according to the present invention, R is methyl, ethyl, n-propyl, i-propyl, n-butyl, s-butyl, t-butyl, i-butyl, 2-methylprop-1-en-2-yl, n-pentyl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl. Any appropriate acylation process leading to the above ketones compounds of formula (5) can be used; as illustrative and non-restricting examples, the acylation is performed in the presence of 2,3-dimethylbutene(s) and a carboxylic acid anhydride, for example acetic anhydride or propionic anhydride. This process step can advantageously be operated in the presence of an acid catalyst.

This process step can advantageously be operated in the presence of a Lewis or Brønsted acid catalyst, for example zinc chloride, methanesulfonic acid, trifluoromethanesulfonic acid, etc. This process step can advantageously be operated either neat or with the use of a suitable aprotic, polar solvent (e.g. dichloromethane).

In an embodiment according to the present invention, the acylation step is preferably followed by an alkylation step; e.g. the 2,3-dimethylbutene(s) are subjected to an acylation synthesis step to form the lower alkyl ketone compounds which are then converted into the desired higher alkyl ketones. In an embodiment according to the present invention, the acylation step is preferably followed by an alkylation step; e.g. the 2,3-dimethylbutene(s) are subjected to an acylation synthesis step to form the compounds of formula (5a) as represented by the following formula (5a, i.e. wherein R=CH₃)

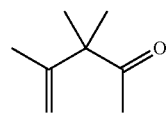

5a which is then converted into compounds of formula (5b) as represented by the following formula

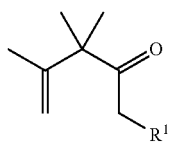

5b wherein R¹ is selected from an alkyl group having from 1 to 5 carbon atoms, an alkenyl group containing only one carbon-carbon double bond and having up to 5 carbon atoms, OR an oxo-alkyl group having up to 5 carbon atoms.

Compound of the formula (5b) which can be obtained either by subjecting 2,3-dimethylbutene(s) to an acylation synthesis step to form directly the compounds of formula (5b) or by subjecting compounds of formula (5a) to an alkylation step can be further alkylated to form compound of formula (5c).

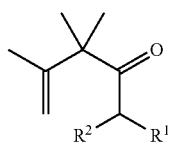

5c wherein R¹ is selected from an alkyl group having from 1 to 4 carbon atoms, an alkenyl group containing only one carbon-carbon double bond and having up to 4 carbon atoms, an oxo-alkyl group having up to 4 carbon atoms, and R² is selected from an alkyl group having from 1 to 4 carbon atoms, an alkenyl group containing only one carbon-carbon double bond and having up to 4 carbon atoms, an oxo-alkyl group having up to 4 carbon atoms, and the sum of carbon atoms present in radicals R¹ and R² is not more than 5.

Compound of the formula (5c) which can be obtained either by subjecting 2,3-dimethylbutene(s) to an acylation synthesis step to form directly the compounds of formula (5c) or by subjecting compounds of formula (5b) to an alkylation step or by subjecting compound (5a) to a double alkylation step can be further alkylated to form compound of formula (5d).

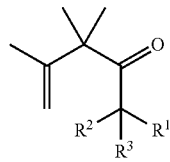

5d wherein R¹ an alkyl group having from 1 to 3 carbon atoms, an alkenyl group containing only one carbon-carbon double bond and having up to 3 carbon atoms, an oxo-alkyl group having up to 3 carbon atoms, and R² is selected from an alkyl group having from 1 to 3 carbon atoms, an alkenyl group containing only one carbon-carbon double bond and having up to 3 carbon atoms, or an oxo-alkyl group having up to 3 carbon atoms, R³ is selected from an alkyl group having from 1 to 3 carbon atoms, an alkenyl group containing only one carbon-carbon double bond and having up to 3 carbon atoms, or an oxo-alkyl group having up to 3 carbon atoms, and the sum of carbon atoms present in radicals R¹, R² and R² is not more than 5.

When compounds of formula (5c) and (5d) have at least two of the R¹, R² or R³ groups identical, the introduction of these identical groups can be performed in a single alkylation step.

An advantage of the acylation step of the synthesis process of the present invention—when 2,3-dimethyl-2-butene is the starting material—is that it can tolerate the presence of 2,3-dimethyl-1-butene. Consequently, whilst the present invention preferentially uses pure 2,3-dimethyl-2-butene for the acylation step, it can also advantageously tolerate as starting materials molar ratios of 2,3-dimethyl-2-butene to 2,3-dimethyl-1-butene which is lower than 99%, for example lower than 95%; said molar ratio is preferably higher than 50%, for example higher than 75%, or even higher than 85%.

In another embodiment according to the present invention, the acylation step is preferably performed starting from pure 2,3-dimethylbut-1-ene.

In an alternative embodiment according to the present invention, the acylation step is preferably followed by an aldol condensation step; e.g. the 2,3-dimethylbutene(s) are subjected to an acylation synthesis step to form the compounds of formula (5a) as represented by the following formula (5a, i.e. wherein R=CH₃)

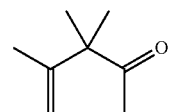

5a which is then converted into compounds of formula (5e) as represented by the following formula

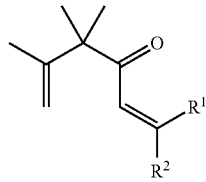

5e wherein R¹ is selected from hydrogen, an alkyl group having from 1 to 4 carbon atoms, an oxo-alkyl group having up to 5 carbon atoms, and R² is selected from hydrogen, an alkyl group having from 1 to 4 carbon atoms, an oxo-alkyl group having up to 4 carbon atoms, and the sum of carbon atoms present in radicals R¹ and R² is not more than 4.

In an embodiment of the present invention, compound of the formula (5b) which can be obtained either by subjecting 2,3-dimethylbutene(s) to an acylation synthesis step to form directly the compounds of formula (5b) or by subjecting compounds of formula (5a) to an alkylation step can be subjected to an aldol condensation step to form compound of formula (5f).

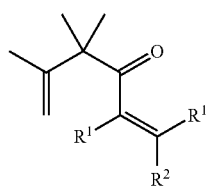

5f wherein R¹ is selected from hydrogen, an alkyl group having from 1 to 4 carbon atoms, an oxo-alkyl group having up to 4 carbon atoms, and R² is selected from hydrogen, an alkyl group having from 1 to 4 carbon atoms, an oxo-alkyl group having up to 4 carbon atoms, and R³ is selected from hydrogen, an alkyl group having from 1 to 4 carbon atoms, an oxo-alkyl group having up to 4 carbon atoms, and the sum of carbon atoms present in radicals R¹ and R² and R³ is not more than 4.

In an embodiment according to the present invention, the acylation step is preferably followed by hydrogenation step and an optional alkylation step; e.g. the 2,3-dimethylbutene(s) are subjected to an acylation synthesis step followed by hydrogenation synthesis step to form the saturated ketones of formula (6) according to the present invention.

In an embodiment according to the present invention, the acylation step is preferably followed by hydrogenation step and an alkylation step; e.g. the 2,3-dimethylbutene(s) are subjected to an acylation synthesis step followed by hydrogenation synthesis step to form the compounds of formula (6a) as represented by the following formula (6a, i.e. wherein R=CH₃)

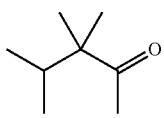

6a which is then converted into compounds of formula (6b) as represented by the following formula

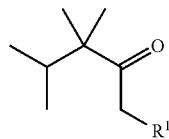

6b wherein $R^1$ is selected from an alkyl group having from 1 to 5 carbon atoms, an alkenyl group containing only one carbon-carbon double bond and having up to 5 carbon atoms, or an oxo-alkyl group having up to 5 carbon atoms.

In an embodiment of the present invention, compound of the formula (5b) which can be obtained either by subjecting 2,3-dimethylbutene(s) to an acylation synthesis step to form directly the compounds of formula (5b) or by subjecting compounds of formula (6a) to an alkylation step can be further alkylated to form compound of formula (6c).

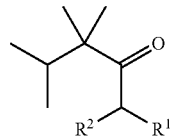

6c wherein $R^1$ is selected from an alkyl group having from 1 to 4 carbon atoms, an alkenyl group containing only one carbon-carbon double bond and having up to 4 carbon atoms, an oxo-alkyl group having up to 4 carbon atoms, and $R^2$ is selected from an alkyl group having from 1 to 4 carbon atoms, an alkenyl group containing only one carbon-carbon double bond and having up to 4 carbon atoms, an oxo-alkyl group having up to 4 carbon atoms, and the sum of carbon atoms present in radicals $R^1$ and $R^2$ is not more than 5.

In an embodiment of the present invention, compound of the formula (6c) which can be obtained either by subjecting 2,3-dimethylbutene(s) to an acylation synthesis step to form directly the compounds of formula (6c) or by subjecting compounds of formula (6b) to an alkylation step or by subjecting compound (6a) to a double alkylation step can be further alkylated to form compound of formula (6d).

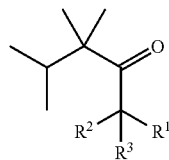

6d wherein $R^1$ an alkyl group having from 1 to 3 carbon atoms, an alkenyl group containing only one carbon-carbon double bond and having up to 3 carbon atoms, or an oxo-alkyl group having up to 3 carbon atoms, and $R^2$ is selected from an alkyl group having from 1 to 3 carbon atoms, an alkenyl group containing only one carbon-carbon double bond and having up to 3 carbon atoms, or an oxo-alkyl group having up to 3 carbon atoms, $R^3$ is selected from an alkyl group having from 1 to 3 carbon atoms, an alkenyl group containing only one carbon-carbon double bond and having up to 3 carbon atoms, or an oxo-alkyl group having up to 3 carbon atoms, and the sum of carbon atoms present in radicals $R^1$, $R^2$ and $R^2$ is not more than 5.

When compounds of formula (6c) and (6d) have at least two of the $R^1$, $R^2$ or $R^3$ groups identical, the introduction of these identical groups can be performed in a single alkylation step.

In an embodiment according to the present invention, the acylation step followed by a hydrogenation step is preferably followed by an aldol condensation step; e.g. the 2,3-dimethylbutene(s) are subjected to an acylation synthesis step followed by a hydrogenation step to form the compounds of formula (6a) as represented by the following formula (6a, i.e. wherein $R=CH_3$)

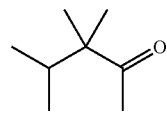

6a which is then converted into compounds of formula (6e) as represented by the following formula

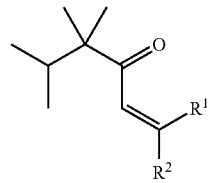

6e wherein $R^1$ is selected from hydrogen, an alkyl group having from 1 to 4 carbon atoms, or an oxo-alkyl group having up to 4 carbon atoms, and $R^2$ is selected from hydrogen, an alkyl group having from 1 to 4 carbon atoms, or an oxo-alkyl group having up to 4 carbon atoms, and the sum of carbon atoms present in radicals $R^1$ and $R^2$ is not more than 4.

In an embodiment according to the present invention, compound of the formula (6b) which can be obtained either by subjecting 2,3-dimethylbutene(s) to an acylation synthesis step to form directly the compounds of formula (6b) or by subjecting compounds of formula (6a) to an alkylation step can be subjected to an aldol condensation step to form compound of formula (6f).

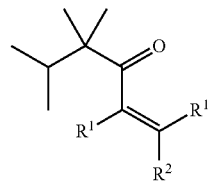

6f wherein $R^1$ is selected from hydrogen, an alkyl group having from 1 to 4 carbon atoms, or an oxo-alkyl group having up to 4 carbon atoms, and $R^2$ is selected from hydrogen, an alkyl group having from 1 to 4 carbon atoms, or an oxo-alkyl group having up to 4 carbon atoms, and $R^3$ is selected from hydrogen, an alkyl group having from 1 to 4 carbon atoms, or an oxo-alkyl group having up to 4 carbon atoms, and the sum of carbon atoms present in radicals $R^1$ and $R^2$ and $R^3$ is not more than 4.

The synthesis of ketones (5) and (6) can be thus advantageously realized according to the following schemes:

illustrative and non-restricting examples, the alkylation is performed in the presence of the products of acylation of 2,3-dimethylbutenes with the general structure (5) or (6) and an alkyl halide or alkyl sulfate (methyl iodide, dimethyl sulfate, etc) in the presence of a base (potassium hydroxide, potassium tertbutoxide, etc). Any appropriate aldol condensation process leading to compounds of formula (5e-f) and (6e-f) respectively can be used; as illustrative and non-restricting examples, the aldol condensation is performed in

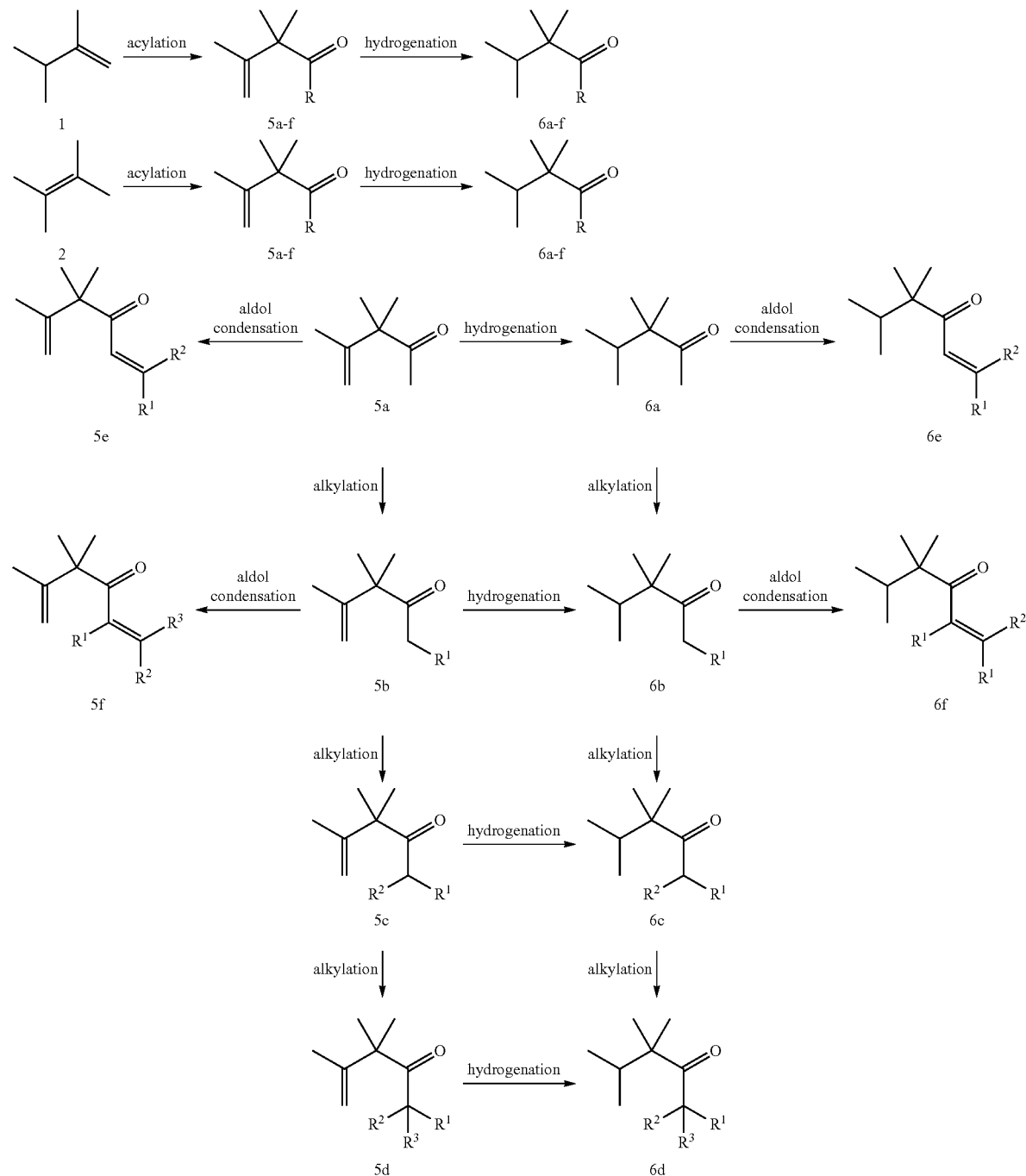

Any appropriate alkylation process leading to compounds of formula (5b-d) and (6b-d) respectively can be used; as the presence of the products of acylation of 2,3-dimethylbutenes with the general structure (5) or (6) and an aldehyde or ketone in the presence of a base (potassium hydroxide, potassium tertbutoxide, etc) or in the presence of an acid (hydrochloric acid, sulfuric acid etc.).

The synthesis of saturated ketones can be thus advantageously realized according to the following scheme:

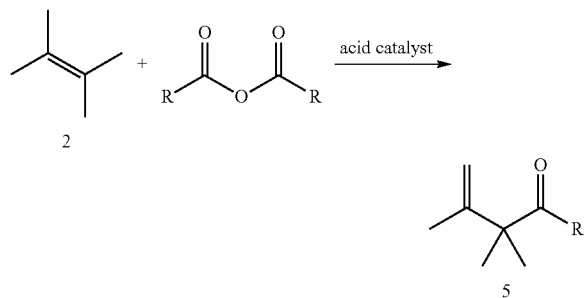

In an embodiment according to the present invention, the compounds of formula (7) can advantageously be prepared by the following consecutive steps:
  Subjecting 2,3-dimethylbutene(s) to an acylation synthesis step, optionally followed by an alkylation step, to form unsaturated ketones compounds (5), and
  Subjecting the unsaturated ketones compounds to a reduction step to form the alcohol compounds of formula (7).

In an embodiment according to the present invention, the compounds of formula (8) can advantageously be prepared by the following consecutive steps:
  Subjecting 2,3-dimethylbutene(s) to an acylation synthesis step, optionally followed by an alkylation step, to form unsaturated ketones compounds (5), and
  subjecting the unsaturated ketones compounds (5) to a hydrogenation step to form the saturated ketones compounds (6)

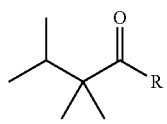

which are then subjected to reduction step to form the alcohol compounds of formula).

An advantage of the carbonyl reduction step of the synthesis process of the present invention is that it can tolerate the presence of the reactants of the previous synthesis step, i.e. the reactants coming either from the acylation step and/or from the combined acylation/alkylation or from the combined acylation/aldol condensation step as described hereinabove.

Consequently, in an embodiment of the present invention, the acylation step can advantageously be performed when
  the molar ratio of 2,3-dimethyl-2-butene to the intermediate ketones is higher than 0, for example higher than 0.05; and/or
  the molar ratio of carboxylic acid anhydride or of Lewis acid (such as aluminum trichloride and/or zinc chloride) coming from the acylation to the intermediate ketones is higher than 0, for example higher than 0.05; and/or
  the molar ratio of catalyst residue coming from the acylation step to the intermediate ketones is higher than 0, for example higher than 0.05.

In an embodiment of the present invention, the carbonyl reduction step can also advantageously be performed when
  the molar ratio of 2,3-dimethyl-2-butene to the intermediate ketones is lower than 0.2, for example lower than 0.15; and/or
  the molar ratio of carboxylic acid anhydride coming from the acylation step to the intermediate ketones is lower than 0.2, for example lower than 0.15; and/or
  the molar ratio of catalyst residue coming from the acylation step to the intermediate ketones is lower than 0.2, for example lower than 0.15.

In an embodiment of the present invention, the claimed fragrance, flavor and/or deodorizing/masking composition is advantageously used as a perfumery composition. Perfumery compositions according to the present invention generally include a perfume, a cologne, an eau du toilette, and/or an eau de parfum. In an embodiment of the present invention, the claimed fragrance, flavor and/or deodorizing/masking composition is advantageously used in a cosmetic formulation, a personal care product, a cleansing product, a fabric softener, and/or air freshener, and the like. Furthermore, it is within the purview of embodiments of the invention that the novel fragrance, flavor and/or deodorizing/masking composition(s) and/or novel compound(s) of formula (7) or of formula (8) described herein may be integrated into building materials, wall and floor coverings, vehicle components, and the like.

In general, in addition to the novel odorant and/or fragrance, flavor and/or deodorizing/masking compositions described herein, suitable fragrance, flavor or deodorizing compositions may advantageously include conventional ingredients such as, for example, solvents, carriers, stabilizers, emulsifiers, moisturizers, dispersants, diluents, thickeners, thinners, other odorants, and/or adjuvants, and the like.

The compounds of formula (7) and/or (8) combine with numerous known natural or synthetic fragrance, flavor and/or deodorizing/masking materials, whereby the range of the natural ingredients can embrace not only readily-volatile but also semi-volatile and slightly-volatile components and the range of the synthetic ingredients can embrace representatives from many classes of substances, as will be evident from the following nonlimitting compilation: Natural products such as:
  Ajowan oil, Amyris oil, Armoise oil, Artemisia oil, Basil oil, Bees wax absolute, Bergamot oil, Birch tar oil, Black pepper oil, Black pepper oleoresin, Camphor oil, Cananga oil, Caraway oil, Cardamom oil, Carrot seed oil, Castoreum absolute, Cedar leaf oil, Cedarwood oil, Celery seed oil, Chamomile oil, Cinnamon bark oil, Cinnamon leaf oil, Cistus absolute, Cistus oil, Citronella oil, Citronella terpenes, Clary sage oil, Clove oil rectified, Cognac oil white, Coriander seed oil, Cumin seed oil, Cypress oil, Davana oil, Dill seed oil, Elemi oil, Elemi resinoid, Eucalyptus oil, Fir needle oil, Galbanum oil, Geranium oil, Ginger oil Indian, Grapefruit oil, Guaiacwood oil, Gurjun balsam, Jasmin absolute, Jatamansi oil, Juniper berry oil, Juniper leaf oil, Kachur oil, Labdanum absolute, Labdanum resinoid, Lavender oil, Lemon oil, Lemon oil terpenes, Lemongrass oil, Lime oil, Litsea cubeba oil, Litsea cubeba terpenes, Lobhan choya resinoid, Mandarin oil, Mentha arvensis oil, Mentha citrata oil, Mimosa absolute, Myrrh resinoid, Nagarmotha oil, Nutmeg oil, Oakmoss absolute, Oakmoss resinoid, Olibanum oil, Olibanum resinoid, Orange oil, Origanum oil, Palma rosa oil, Patchouli oil, Peppermint oil, Peru Balsam resinoid, Petitgrain oil, Pine needle oil, Pink pepper oil, Rose absolut, Rose oil, Rosemary oil, Sandalwood oil, Seaweed absolute, Spearmint oil, Sugandh kokila oil, Sugandh mantri oil, Tagete oil, Tolu Balsam resinoid, Tuberose absolute, Turmeric oil, Turpentine oil, Valerian oil, Vetiver oil, Vetiver terpenes.

Synthetic raw materials for instance:

Esters such as: Aldehyde C16, Allyl amyl glycolate, Allyl caproate, Allyl cyclohexyl propionate, Allyl heptoate, Allyl phenoxy acetate, Amyl acetate iso, Amyl benzoate, Amyl butyrate, Amyl caproate, Amyl cinnamate, Amyl isovalerate, Amyl phenyl acetate, Amyl propionate, Amyl salicylate iso, Amyris acetate, Anisyl acetate, Benzyl acetate, Benzyl benzoate, Benzyl butyrate, Benzyl cinnamate, Benzyl formate, Benzyl isobutyrate, Benzyl isocugenol, Benzyl propionate, Benzyl salicylate, Benzyl tiglate, Butyl acetate, Butyl butyrate, Butyl butyryl lactate, Caryophyllene acetate, Cedryl acetate, Cinnamyl acetate, Cinnamyl butyrate, Cis-3-hexenyl acetate, Cis-3-hexenyl benzoate, Cis-3-hexenyl caproate, Cis-3-hexenyl formate, Cis-3-hexenyl isobutyrate, Cis-3-hexenyl-2-methyl butyrate, Cis-3-hexenyl propionate, Cis-3-hexenyl salicylate, Cis-3-hexenyl tiglate, Citronellyl acetate, Citronellyl butyrate, Citronellyl formnate, Citronellyl isobutyrate, Citronellyl propionate, Citronellyl tiglate, Cyclabute, Cyclogalbanate, Cyclohexyl ethyl acetate, Decyl acetate, Dibutyl phthalate, Diethyl malonate, Diethyl phthalate, Dihydromyrcenyl acetate, Dimethyl octanyl acetate, Dimethyl phenyl ethyl carbinyl acetate, Dioctyl adipate, Dioctyl phthalate, Dimethyl benzyl carbinyl acetate, Dimethyl benzyl carbinyl butyrate, Ethyl linalyl acetate, Ethyl 2-methyl butyrate, Ethyl 3-phenyl propionate, Ethyl acetate, Ethyl acetoacetate, Ethyl benzoate, Ethyl butyrate, Ethyl caprate C10, Ethyl caproate C6, Ethyl caprylate C8, Ethyl cinnamate, Ethyl heptoate, Ethyl hexyl acetate, Ethyl isobutyrate, Ethyl laurate, Ethyl pelargonate, Ethyl phenoxy acetate, Ethyl phenyl acetate, Ethyl phenyl glycidate, Ethyl propionate, Ethyl safranate, Ethyl salicylate, Ethyl valerate, Eugenyl acetate, Evemyl, Fenchyl acetate, Floramat, Frescolat ML, Fructone, Fruitate, Geranyl acetate, Geranyl butyrate, Geranyl formate, Geranyl propionate, Geranyl tiglate, Givescone, Guaiol acetate, Hedionate, Hedione, Helvetolide, Herbanate, Hexyl acetate, Hexyl benzoate, n-Hexyl butyrate, Hexyl caproate, Hexyl isobutyrate, Hexyl propionate, Hexyl salicylate, Isobornyl acetate, Isobutyl acetate, Isobutyl phenyl acetate, Isobutyl salicylate, Isoeugenyl acetate, Isononyl acetate, Isopentyrate, Isopropyl 2-methyl butyrate, Isopropyl myristate, Jasmonyl, Lifarome, Linalyl acetate, Mahagonate, Manzanate, Menthanyl acetate, Menthyl acetate, Methyl benzoate, 2-Methyl butyl acetate, Methyl camomille, Methyl cinnamate, Methyl cyclogeranate, Methyl heptine carbonate, Methyl laurate, Methyl octine carbonate, Methyl phenyl acetate, Methyl salicylate, Methyl-2-methyl butyrate, Neofolione, Nopyl acetate, Octenyl acetate, Octyl acetate, Octyl isobutyrate, Para cresyl acetate, Para cresyl isobutyrate, Para cresyl phenyl acetate, Pear ester, Peranat, Phenoxy ethyl isobutyrate, Phenyl ethyl acetate, Phenyl ethyl butyrate, Phenyl ethyl formate, Phenyl ethyl isobutyrate, Phenyl ethyl phenyl acetate, Phenyl ethyl propionate, Phenyl ethyl salicylate, Phenyl ethyl tiglate, Phenyl propyl isobutyrate, Prenyl acetate, Romandolide, Sagecete, Styrallyl acetate, Styrallyl propionate, Tangerinol, Terpinyl acetate, Thesaron, Trans-2-hexenyl acetate, Tropicate, Verdox, Verdyl acetate, Verdyl propionate, Vertenex, Vetikol acetate, Vetiveryl acetate, Yasmolys.

Lactones such as: Ambrettolide, Arova N, Celeriax, Decalactone delta, Decalactone gamma, Dodecalactone delta, Dodecalactone gamma, Ethylene brassylate, Exaltolide, Heptalactone gamma, Hexalactone delta, Hexalactone gamma, Methyl laitone, Methyl octalactone, Nonalactone delta, Nonalactone gamma, Octahydrocoumarine, Octalactone delta, Octalactone gamma, Rootylone, Silvanone supra, Undecalactone delta, Undecalactone gamma, Valerolactone gamma, 10-Oxa HexaDecanolide (OHD musk), Coumarin, Habanolide, Jasmolactone.

Aldehydes such as: Acetaldehyde, Adoxal, Aldehyde C10, Aldehyde C11 iso, Aldehyde C11 moa, Aldehyde C11 undecylenic, Aldehyde C11 undecylic, Aldehyde C12 lauric, Aldehyde C12 MNA, Anisaldehyde, Amyl cinnamaldehyde, Benzaldehyde, Bourgeonal, Campholenaldehyde, Cantonal, Cetonal, Cinnamic aldehyde, Cis-4-decenal, Cis-6-nonenal, Citral, Citronellal, Citronellyl oxyacetaldehyde, Cocal, Cuminaldehyde, Curgix, Cyclal C, Cyclamen aldehyde, Cyclomyral, Cyclovertal, Decenal 9, Dupical, Empetal, Ethyl vanillin, Floralozone, Florhydral, Geraldehyde, Helional, Heliotropin, Heptanal, Hexanal, Hexyl cinnamaldehyde, Hivemal neo, Hydratropaldehyde, Hydroxycitronellal, Intreleven aldehyde, Isobutavan, Isocyclocitral, Isovaleraldehyde, Lilial, Limonenal, Maceal, Mefranal, Melonal, Methyl cinnamaldehyde, Nonadien-al trans-2 cis-6, Nonanal, Octanal, Oncidal, Para tolyl aldehyde, Phenyl acetaldehyde, Phenyl propyl aldehyde, Precyclemone B, Safranal, Salicylaldehyde, Scentenal, Syringa aldehyde, Trans-4-decenal, Trans-2-dodecenal, Trans-2-hexenal, Trans-2-nonenal, Trifernal, Vanillin, Veratraldehyde, Vernaldehyde Ketones such as: Acetanisol, Acetoin, Acetophenone, Aldron, Allyl ionone, Benzophenone, Benzyl acetone, Calone, Camphor, Carvone d-, Carvone l-, Cashmeran, Cedryl methyl ketone, Cepionate, Claritone, Cosmone, Crysolide, Cyclotene, Damascenone, Damascone alpha, Damascone beta, Damascone delta, Damascone gamma, Diacetyl, Dihydro beta ionone, Dihydro isojasmonate, Dimethyl octenone, Dynascone, Ethyl amyl ketone, Ethyl maltol, Fenchone, Filbertone, Geranyl acetone, Globanone, Heptyl cyclopentanone, Ionone alpha, Ionone beta, Ionone pure, Iriswood, Irone alpha, Iso E Super, Isofenchone, Isojasmone T, Isolone K, Isomenthone, Isophorone, Jasmone cis-, Kambernoir, Kephalis, Koavone, Lavendinal, Maltol, Menthone, Methyl acetophenone, Methyl amyl ketone, Methyl heptenone, Methyl hexyl ketone, Methyl ionone gamma, Methyl naphthyl ketone beta, Methyl nonyl ketone, Muscenone, Muscone, Nectaryl, Orinox, OTBC Ketone, Para tertbutylcyclohexanone, Patchwood, Phantolid, Pharaone, Piperitone, Plicatone, Raspberry ketone, Raspberry ketone methyl ether, Safraleine, Spirogalbanone pure, Tonalid, Trimofix O, Veloutone, Vetikon.

Alcoholos such as: Alcohol oxo C13, Amber core, Ambernax, Ambrinol, Amyl vinyl carbinol, Anisic alcohol, Bacdanol, Benzyl alcohol, Butanol, Cedrol crystals, Cinnamic alcohol, Citronellol, Coranol, Decanol, Dimethyl benzyl carbinol, Dimethyl octanol, Dimethyl phenyl ethyl carbinol, Dimetol, Fenchol, Hexanol, Isobornéol, Isobornyl cyclohexanol, Javanol, Keflorol, Kohinool, Lauryl alcohol, Lilyflore, Linalool oxide, Mayol, Menthol, Norlimbanol, Octanol, Osyrol, Para tertbutylcyclohexanol, Phenoxanol, Phenoxyethanol, Phenyl ethyl alcohol, Phenyl propyl alcohol, Propylene glycol, Rosaphen, Rose glycol, Styrallyl alcohol, Tricyclodecane dimethanol, Tetrahydro linalool, Tetrahydro myrcenol, Timberol, Undecavertol, Cis-3-hexenol, Citronellol laevo, Cyclofloranol, Dihydrolinalool, Dihydromyrcenol, Dimyrcetol, Ebanol, Geraniol, Isopulegol, Linalool, Nerol, Nerolidol, Nonadien-ol trans-2 cis-6, Polysantol, Rosalva, Sandalmysore core, Sandalore, Terpinen-4-ol, Terpineol, Trans-2-hexenol Phenols such as: Butylated hydroxyanisole, Dihydroeugenol, Dimethyl hydroquinone, Dimethyl resorcinol, Eugenol pure, Guaiacol, Isoeugenol, Meta cresol, Methyl diantilis, Para cresol, Propenyl guaethol, Thymol, Ultravanil.

Ethers such as: Ambroxan, Anethole, Anther, Benzyl isoamyl ether, Benzyl isopropyl ether, Benzyl isovalerate, Boisiris, Cedramber, Cetalox, Decyl methyl ether, Dibenzyl ether, Dihydro rose oxide, Diphenyl oxide, Doremox, Estragole, Ethyl linalool, Eucalyptol, Galaxolide, Gyrane, Herbavert, Lime oxide, Madrox, Methyl isoeugenol, Naphthyl isobutyl ether beta, Nerol oxide, Nerolin bromelia, Para cresyl butyl ether, Para cresyl methyl ether, Petiole, Phenyl ethyl methyl ether, Rhubafuran, Rose oxide, Rosyrane, Trisamber, Vetylbois K, Yara yara Acetals such as: Acetal CD, Acetal R, Amberketal, Boisambrene forte, Citrathal, 1,1-Diethoxyethane, Emeraldine, Freshopal, Herboxane, Indoflor, Jacinthaflor, Magnolan, Spirambrene, Viridine, Elintaal, Glycolierral, Karanal, Methyl pamplemousse, Hydrocarbons such as: Bisabolene, Camphene, Carene delta 3, Caryophyllene, Cedrene, Cymene para, Dipentene, Diphenyl methane, Isolongifolene, Limonene d-, Longifolene, Myrcene, Naphthalene, Ocimene, Pinene alpha, Pinene beta, Styrene, Terpinene gamma, Terpinolene, 1,3,5-Undecatriene, Verdoracine.

Sulphur compounds such as: Corps cassis, Dibutyl sulphide, Dimethyl sulphide, Exovert, Grapefruit thiol, Oxane, Ribes mercaptan, Sulfurol, Thiocineol.

Nitriles such as: Cinnamyl nitrile, Citronellyl nitrile, Citronitrile, Clonal, Cumin nitrile, Hexyl cyclopentanone, Irisnitrile, Lemonile, Peonile, Tridecyl nitrile, Agrumen nitrile, n-decyl nitrile.

Oximes such as: Buccoxime, Labienoxime, Stemone.

Nitrogen heterocycles such as: 2-acetylpyrazine, 2-acetylpyridine, sec-butylquinoline, Corps racine, 2-ethyl-3,5(or 6)-dimethylpyrazine, Furfuryl pyrrole, Indole, Isobutyl quinoline, 2-Isobutyl-3(or 6)-methoxypyrazine, Isopropyl quinoline, Maritima, p-methyl quinoline, Skatol, 2,3,5-trimethylpyrazine.

Nitro compound such as: Musk Ketone.

Schiff bases such as: Aurantiol, Helianthral, Ligantraal, Verdantiol.

Other materials such as: Acetanilide, Gardamide, Paradisamide, Dimethyl anthranilate, Methyl anthranilate, n-Butyric acid, Capric acid, Caproic acid, Caprylic acid, Phenylacetic acid, Caryophyllene oxide, Cedroxyde, Tobacarol The compounds of formula (7) and/or (8) can accordingly be used for the production of compositions and, as will be evident from the foregoing compilation, a wide range of known odorants/fragrance, flavor and/or deodorizing/masking materials. In the production of such compositions, the known fragrance, flavor and/or deodorizing/masking materials referred to earlier can be used according to methods which are known to the perfumer such as, for example, according to W. A. Poucher, Perfumes, Cosmetics and Soaps 2, 7th Edition, Chapman and Hall, London 1974.

In an embodiment of the present invention, the claimed fragrance, flavor and/or deodorizing/masking composition comprises in addition to the alcohols of formula (7) and/or (8) at least one ester and/or one alcohol, preferably at least a mixture of ester and alcohol; the said ester and/or alcohol are preferably selected from the list defined herein above. In an embodiment of the present invention, the claimed odorant composition is characterized by a total content of the compound(s) of formula (7) or of formula (8) together with the ester(s) and/or other alcohol(s) which is superior to 25 wt %, preferably superior to 50 wt %, for example superior to 75 wt %, or even superior to 90 wt %.

All stereoisomers of the compounds of the instant disclosure are contemplated, either in admixture or in pure or substantially pure form. The compounds of the present disclosure can have asymmetric centers at any of the carbon atoms, consequently, claimed compounds can exist in enantiomeric, or diastereomeric forms, or in mixtures thereof. The processes for preparation can utilize racemates, (pure) enantiomers, nonracemic mixtures of enantiomers, diastereomers or mixtures of diastereomers as starting materials. When diastereomeric or enantiomeric products are obtained as mixtures, they can be separated by conventional methods for example, chromatographic separation or fractional crystallization or through diastereomeric salt formation. When intended, a desired enantiomer or diastereomer can also be obtained by following appropriate enantioselective or diastereoselective reactions.

In an embodiment of the present invention, the claimed fragrance, flavor and/or deodorizing/masking composition comprises in addition to the alcohols of formula (7) or of formula (8) their respective parent ketone of formula (5) or of formula (6).

By parent compound is considered here a compound which is an intermediate used in the synthesis.

The present invention also relates to odorant compositions comprising a mixture of alcohol(s) of formula (7) with its(their) respective parent ketone(s) of formula (5); in a preferred embodiment, the weight ratio between the parent ketone of formula (5) and its alcohol of formula (7) is comprised between 0.001 and 0.2, and/or the total content in the odorant composition of the alcohols of formula (7) and of their respective parent ketone of formula (5) is superior to 1 wt %, e.g. superior to 25 wt %, preferably superior to 50 wt %, for example superior to 75 wt %, or even superior to 90 wt %.

The present invention also relates to odorant compositions comprising a mixture of alcohol(s) of formula (8) with its(their) respective parent ketone(s) of formula (6); in a preferred embodiment, the weight ratio between the parent ketone of formula (6) and its alcohol of formula (8) is comprised between 0.001 and 0.2, and/or the total content in the odorant composition of the alcohols of formula (8) and of their respective parent ketone of formula (6) is superior to 1 wt %, e.g. superior to 25 wt %, preferably superior to 50 wt %, for example superior to 75 wt %, or even superior to 90 wt %.

In another embodiment of the present invention, the claimed fragrance, flavor and/or deodorizing/masking composition comprises a mixture of the alcohols of formula (8) and of the alcohols of formula (7).

The present invention also relates to odorant compositions comprising a mixture of alcohol(s) of formula (7) and alcohol(s) of formula (8), optionally and preferably together with their respective parent ketone of formula (5)/formula (6); in a preferred embodiment, the weight ratio between the parent ketone and its alcohol is comprised between 0.001 and 0.2, and/or the total content in the odorant composition of the alcohols of formula (7) and of formula (8) and of their respective parent ketone of formula (5) and of formula (6) is superior to 1 wt %, e.g. superior to 25 wt %, preferably superior to 50 wt %, for example superior to 75 wt %, or even superior to 90 wt %.

The present invention also relates to odorant compositions comprising a mixture of alcohol of formula (7d) optionally and preferably together with one or more alcohols of formula (7a-c) and/or one or more of their respective parent ketones of formula (5a-d).

The present invention also relates to odorant compositions comprising a mixture of alcohol of formula (7c) optionally and preferably together with one or more alcohols of formula (7a-b) and/or one or more of their respective parent ketones of formula (5a-c).

The present invention also relates to odorant compositions comprising a mixture of alcohol of formula (7b) optionally and preferably together with alcohol of formula (7a) and/or one or more of their respective parent ketones of formula (5a-b).

The present invention also relates to odorant compositions comprising a mixture of alcohol of formula (7e) optionally and preferably together with alcohol of formula (7a) and/or one or more of their respective parent ketones of formula (5a, e).

The present invention also relates to odorant compositions comprising a mixture of alcohol of formula (7) optionally and preferably together with one or more alcohols of formula (7a-b) and/or one or more of their respective parent ketones of formula (5a-b, f).

The present invention also relates to odorant compositions comprising a mixture of alcohol of formula (Be) optionally and preferably together with alcohol of formula (8a) and/or (7a) and/or their respective parent ketones of formula (6a) and/or (5a).

The present invention also relates to odorant compositions comprising a mixture of alcohol of formula (8f) optionally and preferably together with alcohol of formula (8a) and/or (8b) and/or (7a) and/or their respective parent ketones of formula (6f) and/or (6a) and/or (6b) and/or (5a).

The present invention also relates to odorant compositions comprising a mixture of alcohol of formula (8f) optionally and preferably together with alcohol of formula (8b) and/or (7b) and/or (7a) and/or their respective parent ketones of formula (6f) and/or (6b) and/or (5b) and/or (5a).

The present invention also relates to odorant compositions comprising a mixture of alcohol of formula (8c) optionally and preferably together with alcohol of formula (8b) and/or (8a) and/or (7a) and/or their respective parent ketones of formula (6c) and/or (6b) and/or (6a) and/or (5a).

The present invention also relates to odorant compositions comprising a mixture of alcohol of formula (8c) optionally and preferably together with alcohol of formula (8b) and/or (7b) and/or (7a) and/or their respective parent ketones of formula (6c) and/or (6b) and/or (5b) and/or (5a).

The present invention also relates to odorant compositions comprising a mixture of alcohol of formula (8c) optionally and preferably together with alcohol of formula (7c) and/or (7b) and/or (7a) and/or their respective parent ketones of formula (6c) and/or (5c) and/or (5b) and/or (5a).

The present invention also relates to odorant compositions comprising a mixture of alcohol of formula (8d) optionally and preferably together with alcohol of formula (8c) and/or (8b) and/or (8a) and/or (7a) and/or their respective parent ketones of formula (6d) and/or (6c) and/or (6b) and/or (6a) and/or (5a).

The present invention also relates to odorant compositions comprising a mixture of alcohol of formula (8d) optionally and preferably together with alcohol of formula (8c) and/or (8b) and/or (7b) and/or (7a) and/or their respective parent ketones of formula (6d) and/or (6c) and/or (6b) and/or (5b) and/or (5a).

The present invention also relates to odorant compositions comprising a mixture of alcohol of formula (8d) optionally and preferably together with alcohol of formula (8c) and/or (7c) and/or (7b) and/or (7a) and/or their respective parent ketones of formula (6d) and/or (6c) and/or (5c) and/or (5b) and/or (5a).

The present invention also relates to odorant compositions comprising a mixture of alcohol of formula (8d) optionally and preferably together with alcohol of formula (7d) and/or (7c) and/or (7b) and/or (7a) and/or their respective parent ketones of formula (6d) and/or (5d) and/or (5c) and/or (5b) and/or (5a).

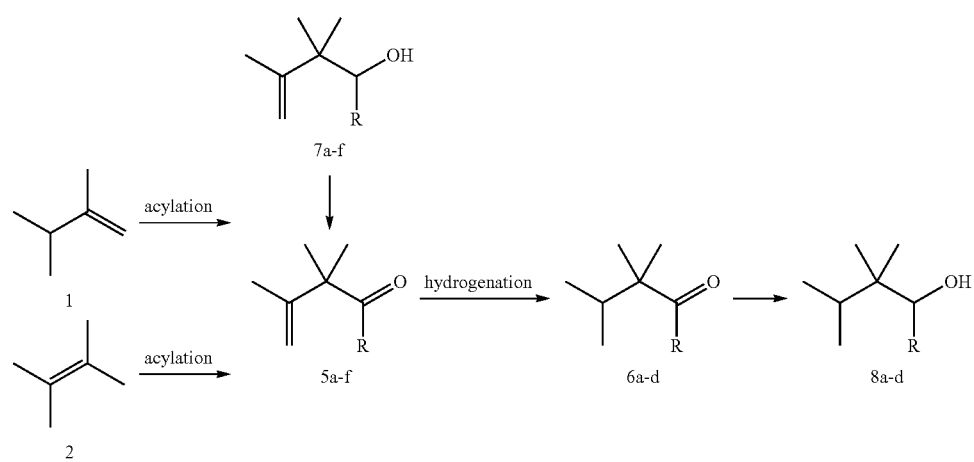

-continued
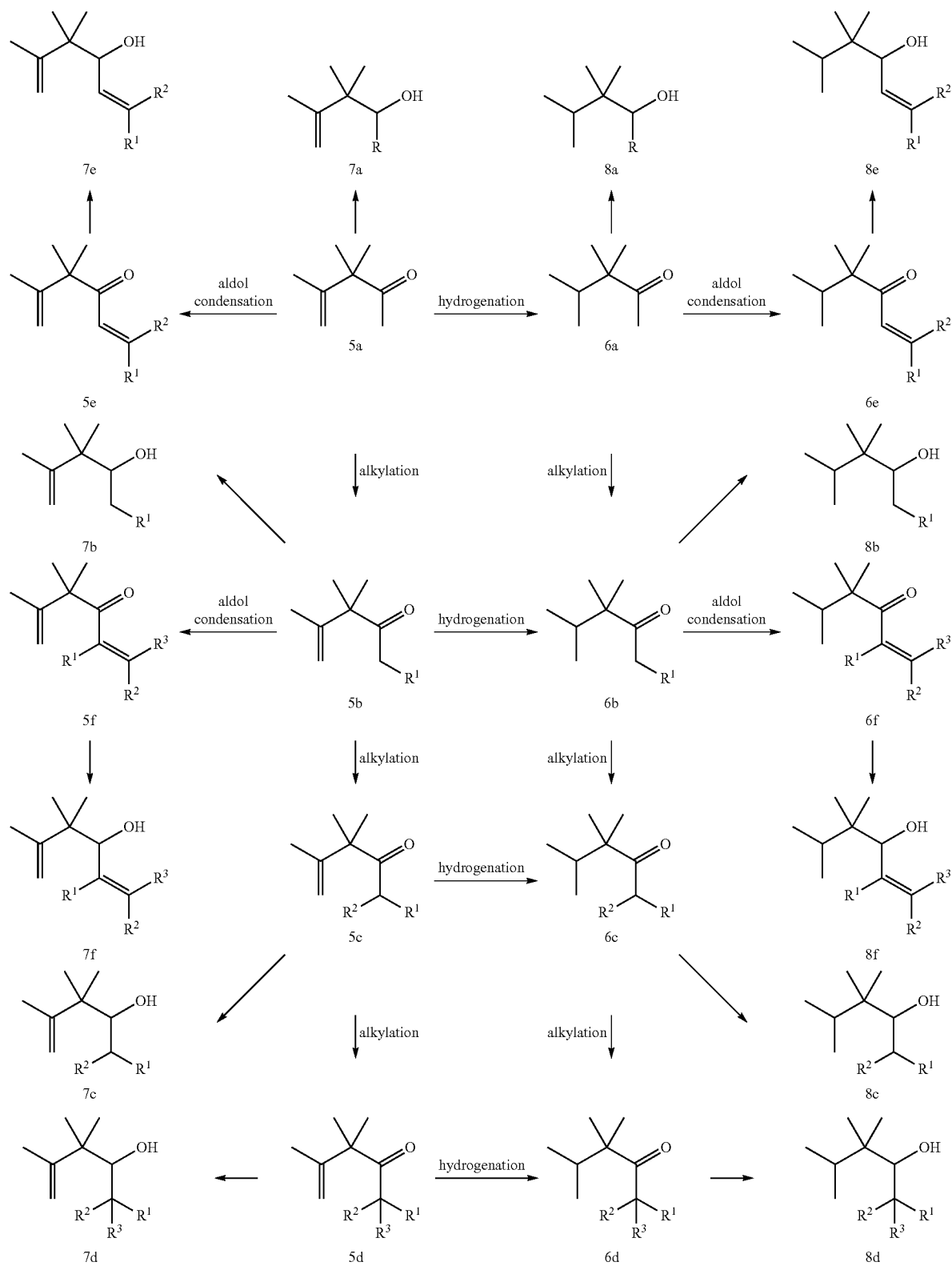

As a reminder, the alcohols of formula (7) and of formula (8) can advantageously be represented by the following schemes

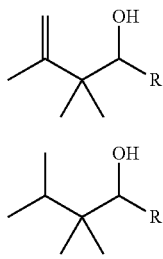

7

8 wherein R is an alkyl group having from 1 to 6 carbon atoms or an alkenyl group having from 2 to 6 carbon atoms.

As a reminder, the ketones of formula (5) or of formula (6) can advantageously be represented by the following schemes

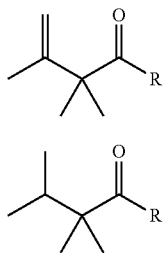

5

6 wherein R is an alkyl group having from 1 to 6 carbon atoms or an alkenyl group having from 2 to 6 carbon atoms.

The disclosure is further illustrated by the following examples which in no way should be construed as being further limiting. One skilled in the art will readily appreciate that the specific methods and results described are merely illustrative.

SYNTHESIS EXAMPLES

Example 1

Synthesis of 4,4,5-trimethylhex-5-en-3-ol

Step-1: Synthesis of 4,4,5-trimethylhex-5-en-3-one

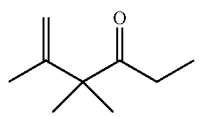

Methanesulfonic acid (886 g, 9.21 mol) was added to a mixture of 2,3-dimethyl-2-butene (2.58 kg, 30.7 mol, 1 equiv) and propionic anhydride (3.99 kg, 30.7 mol) at 25° C., under nitrogen while stirring. The mixture was stirred at 25° C. for 4 h. Subsequently. the mixture was washed with water (1×2.00 L) followed by aqueous 11.7% sodium carbonate solution (1×6.00 kg) and water (1×2.00 L). The crude product was purified by distillation in vacuo to afford 4,4,5-trimethylhex-5-en-3-one (2.20 kg, 51%).

$^1$H NMR (400 MHz, CDCl$_3$): δ 0.92 (t, J=7.2 Hz, 3), 1.15 (s, 61), 1.56 (s, 3), 2.35 (q, J=7.2 Hz, 2H), 4.87 (s, 2H).

$^{13}$C NMR (100 MHz, CDCl$_3$): δ 8.3, 20.1, 23.3, 29.5, 53.5, 111.4, 148.0, 214.4.

Step-2: Synthesis of 4,4,5-trimethylhex-5-en-3-ol

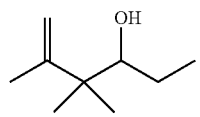

Sodium borohydride (930 g, 24.5 mol) was added to a mixture of 4,4,5-trimethylhex-5-en-3-one (3.00 kg, 21.4 mol) ethanol (6.00 kg) and water (1.50 kg) at 20-25° C. over a period of 4 h while stirring. Then the mixture was stirred for 9 h at 30° C. Subsequently, acetic acid (400 g) was added. Organic phase was separated and washed with water (3×9.00 L), aqueous 10% sodium carbonate solution (1×3.00 L) and water (1×3.00 L). The crude product (2.85 kg) was distilled in vacuo (75-81° C./35 mbar) to afford 4,4,5-trimethylhex-5-en-3-ol (1.97 g, 65%) as a colorless liquid.

$^1$H NMR (600 MHz, CDCl$_3$) δ 1.01 (s, 3H), 1.02 (t, J=7.4 Hz, 3H), 1.05 (s, 3H), 1.26 (tdd, J=14.1, 9.5, 7.3 Hz, 1H), 1.52 (tdd, J=15.1, 7.5, 1.7 Hz, 1H), 1.75 (s, 3H), 3.38 (dd, J=10.4, 1.7 Hz, 1H), 4.84 (s, 1H), 4.91 (s, 1H). $^{13}$C NMR (151 MHz, CDCl$_3$) δ 11.93, 19.72, 21.47, 22.66, 23.92, 43.82, 77.28, 111.90, 151.14.

Example 2

Synthesis of 4,4,5-trimethylhexan-3-ol

Step-1: Synthesis of 4,4,5-trimethylhexan-3-one

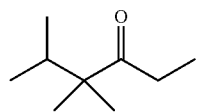

Raney Ni (400 mg, 6.80 mmol) was added to a solution of 4,4,5-trimethylhex-5-en-3-one (50.0 g, 356 mmol) in isopropanol (240 mL) at 25° C. and the mixture was stirred under hydrogen at 60° C./14 bar for 48 h. The mixture was cooled to 25° C., filtered through a pad of celite and the solvent was removed under reduced pressure to afford 4,4,5-trimethylhexan-3-one (47.6 g, 94%).

$^1$H NMR (400 MHz, CDCl$_3$): δ 0.72 (d, J=7.2 Hz, 6H), 0.93-0.97 (m, 9H), 1.90-1.96 (m, 1H), 2.39 (q, J=7.2 Hz, 2H). $^{13}$C NMR (100 MHz, CDCl$_3$): δ 8.0, 17.4, 20.4, 30.0, 33.9, 50.5, 216.8.

Step-2: Synthesis of 4,4,5-trimethylhexan-3-ol

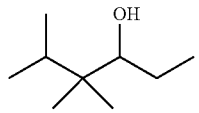

Sodium borohydride (9.50 g, 253 mmol) was added to a mixture of 4,4,5-trimethylhexan-3-one (30.0 g, 210 mmol) in ethanol (60.0 mL) and water (15.0 mL) at 20-25° C. over a period of 1 h while stirring. Then the mixture was stirred for 9 h at 30° C. Subsequently, acetic acid (4.00 g) was added. Organic phase was separated and washed with water (3×90.0 mL), aqueous 10% sodium carbonate solution (1×30.0 mL) and water (1×30.0 mL). The crude product was distilled in vacuo to afford 4,4,5-trimethylhexan-3-ol (27.0 g, 90%) as a colorless liquid.

$^1$H NMR (400 MHz, CDCl$_3$): δ 0.64 (s, 3H), 0.72 (s, 3H), 0.73 (d, J=6.0 Hz, 3H), 0.78 (d, J=6.8 Hz, 3H), 0.93 (t, J=7.2 Hz, 3H), 1.10-1.19 (m, 1H), 1.44-1.54 (m, 1H), 1.62-1.70 (m, 1H), 1.84 (s, 1H), 3.25 (dd, J=10.4 Hz & 1.6 Hz, 1H).
$^{13}$C NMR (100 MHz, CDCl$_3$): δ 10.0, 16.3, 16.5, 16.8, 17.0, 22.0, 30.7, 37.8, 76.8.

Example 3

Synthesis of 33-trimethylpent-4-en-2-ol

Step 1: Synthesis of 3,3,4-trimethylpent-4-en-2-one

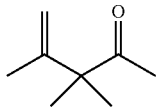

Methanesulfonic acid (171 g, 1.77 mol) was added to a mixture of 2,3-dimethyl-2-butene (510 g, 5.94 mol) and acetic anhydride (520 g, 5.94 mol) at 5° C. under nitrogen while stirring. The mixture was stirred in an ice bath and left to reach 20° C. within 24 h. Subsequently, water (1.50 L) was added and the mixture was extracted with methyl tert-butyl ether (3×500 mL). The combined organic phases were washed successively with water (2×750 mL), aqueous saturated sodium carbonate solution till pH 7 and brine (750 mL). The organic phase was dried over Na$_2$SO$_4$ and volatiles were removed under reduced pressure. The residue (960 g) was distilled in vacuo to afford 3,3,4-trimethylpent-4-en-2-one (501 g, 66%).

$^1$H NMR (400 MHz, CDCl$_3$): δ 1.15 (s, 6H), 1.58 (s, 3H), 1.98 (s, 3H), 4.89 (s, 2H).
$^{13}$C NMR (100 MHz, CDCl$_3$): δ 19.2, 22.2, 23.9, 53.0, 110.6, 146.8, 210.9.

Step 2: Synthesis of 3,3,4-trimethylpent-4-en-2-ol

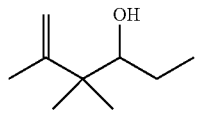

Sodium borohydride (60.0 g, 1.58 mol) was added to a mixture of 3,3,4-trimethylpentan-2-one (200 g, 1.58 mol) in ethanol (400 mL) and water (200 mL) at 20-25° C. for 1 h while stirring. Then the mixture was stirred for 2 h at 30° C. Subsequently, saturated aqueous ammonium chloride solution was added and the mixture was extracted with ethyl acetate (3×300 mL). Mixed extracts were washed with water (3×90.0 mL), aqueous 10% sodium carbonate solution (1×300 mL) and water (1×300 mL). The volatiles were removed under reduced pressure and the residue (285 g) was distilled in vacuo (27-30° C./30 mbar) to afford 3,3,4-trimethylpent-4-en-2-ol (168 g, 83%) as a colorless liquid.

$^1$H NMR (600 MHz, CDCl$_3$): δ 1.00 (s, 3H), 1.05 (s, 3H), 1.10 (d, J=6.4 Hz, 3H), 1.68 (s, 1H), 1.76 (s, 3H), 3.74 (q, J=6.3 Hz, 1H), 4.86 (d, J=0.7 Hz, 1H), 4.96-4.90 (m, 1H).
$^{13}$C NMR (151 MHz, CDCl$_3$) δ 16.6, 19.6, 20.5, 22.7, 43.6, 70.9, 112.0, 150.9.

Example 4

Synthesis of 3,3,4-trimethylpentan-2-ol

Step 1: Synthesis of 3,3,4-trimethylpentan-2-one

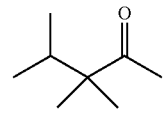

Raney Ni (3.48 g, 59.4 mmol) was added to a solution of 3,3,4-trimethylpent-4-en-2-one (150 g, 1.18 mol) in methanol (300 mL) and the reactor was flushed with nitrogen. Then the mixture was stirred under hydrogen atmosphere at 60° C./21 bar for 72 h. Subsequently, the mixture was cooled to 25° C. and filtered through pad of celite. The filter cake was washed with methanol (100 mL). Combined filtrates were dried over sodium sulphate (152 g) and the volatiles removed under reduced pressure to afford 3,3,4-trimethylpentan-2-one (140 g, 91.8%).

$^1$H NMR (400 MHz, CDCl$_3$): δ 0.75 (d, J=6.8 Hz, 6H), 0.95 (s, 6H), 1.88-1.98 (m, 1H), 2.04 (s, 3H).
$^{13}$C NMR (100 MHz, CDCl$_3$): δ 17.4, 20.2, 25.0, 33.7, 50.8, 214.2.

Step 2: Synthesis of 3,3,4-trimethylpentan-2-ol

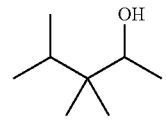

Sodium borohydride (42.3 g, 1.12 mmol) was added to a mixture of 3,3,4-trimethylpentan-2-one (152 g, 1.19 mol), methanol (400 mL) and water (22.8 mL) at 0-5° C. over a period of 1 h while stirring. Then the mixture was stirred at 25° C. for 24 h. Subsequently, sodium borohydride (10.6 g, 280 mmol) was added over a period of 15 min at 25° C. and the mixture stirred for another 21 h. Then, aqueous 10% hydrochloric acid solution was added at 5-10° C. till pH 7. Subsequently, volatiles were removed under reduced pressure, at 50° C. and water (150 mL) was added. The mixture was extracted with dichloromethane (3×150 mL). Combined organic phases were washed with brine (1×100 mL) and dried over sodium sulphate (15 g). Volatiles were removed under reduced pressure at 40° C. to afford 3,3,4-trimethylpentan-2-ol (125 g, 80.7%) as a colorless liquid.

$^1$H NMR (400 MHz, CDCl$_3$): δ 0.63 (s, 3H), 0.73 (s, 3H), 0.76 (d, J=8.0 Hz, 3H), 0.78 (d, J=6.8 Hz, 3H), 1.03 (d, J=6.4 Hz, 3H), 1.55-1.66 (m, 1H), 1.95-1.96 (bs, 1H), 3.66 (q, J=6.4 Hz, 1H).

$^{13}$C NMR (100 MHz, CDCl$_3$): δ 17.2, 17.9, 18.7, 32.5, 39.4, 71.9.

Example 5

Synthesis of Synthesis of 2,3,3-trimethyloct-1-en-4-ol

Step 1: Synthesis of 2,3,3-trimethyloct-1-en-4-one

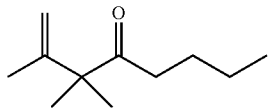

Methane sulfonic acid (48.0 g, 499 mmol) was added to a mixture of valeric anhydride (310 g, 1.66 mol) and 2,3-dimethylbut-2-ene (140 g, 1.66 mol) over a period of 30 min while stirring. Then, the mixture was stirred for 28 h at 40° C. Subsequently, aqueous 15% potassium carbonate solution (1.33 L) was added at 25° C. and the mixture stirred for 30 min. Organic phase was separated and washed with water (4×300 ml) till pH 7. Crude product (204 g) was distilled in vacuo (70-75° C./12 mbar) to afford 2, 3, 3-trimethyloct-1-en-4-one (104 g, 37.1%) as a colorless liquid.

$^1$H NMR (400 MHz, CDCl$_3$): δ 0.81 (t, J=7.2 Hz, 3H), 1.15-1.24 (m, 8H), 1.39-1.46 (m, 2H), 1.57 (s, 3H), 2.32 (t, J=7.6 Hz, 2H), 4.88 (s, 2H).

$^{13}$C NMR (100 MHz, CDCl$_3$): δ 14.0, 20.3, 22.5, 23.4, 26.4, 36.2, 53.8, 111.7, 148.1, 214.0.

Step 2: Synthesis of 2,3,3-trimethyloct-1-en-4-ol

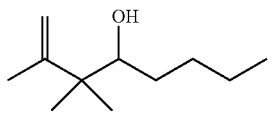

Sodium borohydride (8.57 g, 232 mmol) was added to a solution of 2,3,3-trimethyloct-1-en-4-one (51.0 g, 29.0 mmol) in ethanol (50.0 mL) and THE (50.0 mL) at 30° C. was added over a period of 30 min while stirring. Then the mixture was stirred for 14 h at 65° C. Subsequently, aqueous 5% hydrogen chloride solution (40 mL) was added at 25° C. Organic phase was separated and the aqueous phase was extracted with ethyl acetate (1×200 mL). Combined organic phases were washed with water (4×100 mL) and the volatiles removed under reduced pressure. Crude product (49.0 g) was distilled in vacuo (85-89° C./10 mbar) to afford 2,3,3-trimethyloct-1-en-4-ol (42.9 g, 87.1%) as a colorless liquid.

$^1$H NMR (600 MHz, CDCl$_3$): δ 0.91 (t, J=7.2 Hz, 3H), 1.01 (s, 3H), 1.05 (s, 3H), 1.39-1.21 (m, 4H), 1.47-1.41 (m, 1H), 1.62-1.52 (m, 2H), 1.75 (s, 3H), 3.48-3.44 (m, 1H), 4.84 (s, 1H), 4.91 (s, 1H).

$^{13}$C NMR (151 MHz, CDCl$_3$): δ 14.1, 19.7, 21.4, 22.6, 22.8, 29.6, 30.7, 43.8, 75.5, 111.9, 151.1.

Example 6

Synthesis of 2.3.3-trimethyloctan-4-ol

Step-1: Synthesis of 2,3,3-trimethyloctan-4-one

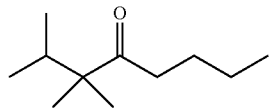

Raney Ni (1.93 g, 32.0 mmol) was added to a solution of 2,3,3-trimethyloct-1-en-4-one (120 g, 660 mmol) in isopropanol (200 mL) and the autoclave was flushed with nitrogen. Then the mixture was stirred under hydrogen atmosphere at 50° C./7 bar for 13 h. The mixture was cooled to 25° C., filtered through a pad of celite and the filter cake was washed with isopropanol (50 mL). The filtrate was dried over sodium sulphate (152 g) and volatiles removed under reduced pressure to afford 2,3,3-trimethyloctan-4-one (105 g, 83%) as a colorless liquid.

$^1$H NMR (400 MHz, CDCl$_3$): δ 0.72 (d, J=7.2 Hz, 6H), 0.83 (t, J=7.6 Hz, 3H), 0.93 (s, 6H), 1.13-1.27 (m, 2H), 1.42-1.49 (m, 2H), 1.90-1.97 (m, 1H), 2.36 (t, J=7.6 Hz, 2H).

$^{13}$C NMR (100 MHz, CDCl$_3$): δ 13.9, 17.5, 20.3, 22.4, 26.0, 33.7, 36.6, 50.6, 216.3.

Step-2: Synthesis of 2,3,3-trimethyloctan-4-ol

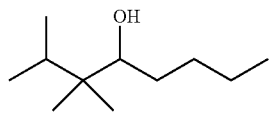

Sodium borohydride (6.48 g, 175 mmol) was added to a solution of 2,3,3-trimethyloctan-4-one (42.0 g, 219 mmol) in ethanol (150 ml) at 30° C. over a period of 30 min while stirring. Then the mixture was stirred for 12 h at 75° C. Subsequently, ethyl acetate (200 ml) was added at 30° C. followed by aqueous 0.5 N hydrogen chloride solution (40 ml). Organic phase was separated, washed with water (4×100 mL) and volatiles removed under reduced pressure to afford 2,3,3-trimethyloctan-4-ol (39.5 g, 97%)

$^1$H NMR (600 MHz, CDCl$_3$): δ 3.44 (d, J=7.9 Hz, 1H), 1.77-1.67 (m, 1H), 1.61-1.47 (m, 2H), 1.41-1.19 (m, 6H), 0.92 (t, J=7.2 Hz, 3H), 0.86 (d, J=6.9 Hz, 3H), 0.82 (d, J=6.9 Hz, 3H), 0.81 (s, 3H), 0.72 (s, 3H).

$^{13}$C NMR (151 MHz, CDCl$_3$): δ 14.1, 17.2, 17.6, 18.4, 18.8, 22.8, 29.4, 30.9, 32.8, 39.5, 76.8.

Example 7

Synthesis of 2,3,3-trimethylnon-1-en-4-ol

Step-1: Synthesis of 2,3,3-trimethylnon-1-en-4-one

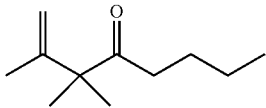

Methane sulfonic acid (27.9 g, 290 mmol) was added to a mixture of caproic anhydride (208 g, 970 mmol) and 2,3-dimethylbut-2-ene (85.5 g, 970 mmol) over a period of 30 min while stirring. Then the mixture was stirred for 18 h at 40° C. Subsequently, aqueous 15% sodium carbonate solution (60.0 g) was added at 25° C. and the mixture was stirred for 30 min. Organic phase was separated and the aqueous phase extracted with ethyl acetate (2×300 mL). Combined organic phases were washed with water (4×300 ml) till pH 7 and volatiles removed under reduced pressure. Crude product was distilled in vacuo (75-84° C./6 mbar) to afford 2,3,3-trimethylnon-1-en-4-one (68.2 g, 38.5%).

$^1$H NMR (400 MHz, CDCl$_3$): δ 0.80 (t, J=7.2 Hz, 3H), 1.15-1.25 (m, 10H), 1.40-1.48 (m, 2H), 1.56 (s, 3H), 2.32 (t, J=7.6 Hz, 2H), 4.87 (s, 2H).

$^{13}$C NMR (100 MHz, CDCl$_3$): δ 14.0, 20.3, 22.6, 23.4, 23.9, 31.6, 36.4, 53.8, 111.7, 148.1, 214.0.

Step-2: Synthesis of 2,3,3-trimethylnon-1-en-4-ol

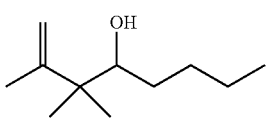

Sodium borohydride (4.03 g, 109 mmol) was added to a solution of 2,3,3-trimethylnon-1-en-4-one (35.0 g, 182 mmol) in ethanol (90.0 ml) at 30° C. over a period of 30 min while stirring. Then the mixture was stirred for 9 h at 65° C. Subsequently, ethyl acetate (150 ml) was added at 30° C. followed by aqueous 0.5 N hydrogen chloride solution (40.0 ml). Separated organic phase was washed with water (4×80.0 mL) and the volatiles removed under reduced pressure to afford 2,3,3-trimethylnon-1-en-4-ol (34.0 g, 96%) as a colorless liquid.

$^1$H NMR (600 MHz, CDCl$_3$): δ 0.90 (t, J=7.0 Hz, 3H), 1.01 (s, 3H), 1.05 (s, 3H), 1.36-1.21 (m, 6H), 1.46-1.40 (m, 1H), 1.54 (s, J=18.5 Hz, 1H), 1.63-1.56 (m, 1H), 1.75 (d, J=0.7 Hz, 3H), 3.48-3.44 (m, 1H), 4.84 (d, J=0.9 Hz, 1H), 4.93-4.89 (m, 1H).

$^{13}$C NMR (151 MHz, CDCl$_3$): δ 14.10, 19.71, 21.47, 22.61, 22.73, 27.13, 31.01, 32.03, 43.79, 75.53, 111.91, 151.13.

Example 8

Synthesis of 2,3,3-trimethylnonan-4-ol

Step-1: Synthesis of 2,3,3-trimethylnonan-4-one

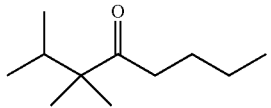

Raney Ni (2.03 g, 34.0 mmol) was added to a solution of 2,3,3-trimethylnon-1-en-4-one (135 g, 690 mmol) in isopropanol (207 mL) and the autoclave was flushed with nitrogen. Then the mixture was stirred under hydrogen atmosphere at 50° C./7 bar for 5 h. The mixture was cooled to 25° C. and filtered through a pad of celite. The filter cake was washed with isopropanol (50.0 mL). The combined filtrates were dried over sodium sulphate (150 g) and volatiles removed under reduced pressure to afford 2,3,3-trimethyloctan-4-one (128 g, 94.8%) as a colorless liquid.

$^1$H NMR (400 MHz, CDCl$_3$): δ 0.73 (d, J=6.8 Hz, 6H), 0.81 (t, J=7.2 Hz, 3H), 0.93 (s, 6H), 1.13-1.27 (m, 4H), 1.44-1.51 (m, 2H), 1.90-1.97 (m, 1H), 2.35 (t, J=7.6 Hz, 2H).

$^{13}$C NMR (100 MHz, CDCl$_3$): δ 13.8, 17.4, 20.3, 22.5, 23.5, 31.5, 33.7, 36.8, 50.5, 216.1.

Step-2: Synthesis of 2,3,3-trimethylnonan-4-ol

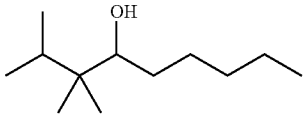

Sodium borohydride (13.6 g, 369 mmol) was added to a solution of 2,3,3-trimethylnonan-4-one (60.0 g, 307 mmol) in ethanol (225 ml) at 30° C. over a period of 30 min while stirring. Then the mixture was stirred for 29 h at 78° C. Subsequently, ethyl acetate (300 ml) was added at 30° C. followed by aqueous 0.5 N solution of hydrogen chloride (60.0 ml). Separated organic phase was washed with water (4×150 mL) and volatiles removed under reduced pressure. Crude product was distilled in vacuo (90-103° C./11 mbar) to afford 2,3,3-trimethylnonan-4-ol (50.8 g, 89%) as a colorless liquid.

$^1$H NMR (600 MHz, CDCl$_3$) δ 0.72 (s, 3H), 0.81 (s, 3H), 0.82 (d, J=6.9 Hz, 3H), 0.86 (d, J=6.9 Hz, 3H), 0.90 (t, J=7.0 Hz, 3H), 1.38-1.19 (m, 7H), 1.49 (ddd, J=9.2, 6.3, 2.4 Hz, 1H), 1.63-1.53 (m, 1H), 1.77-1.68 (m, 1H), 3.47-3.41 (m, 1H).

$^{13}$C NMR (151 MHz, CDCl$_3$) δ 14.1, 17.2, 17.6, 18.4, 18.8, 22.7, 26.9, 31.2, 32.0, 32.8, 39.5, 76.9.

Example 9

Synthesis of 2,4,4,5-tetramethylhex-5-en-3-ol

Step-1: Synthesis of 2,4,4,5-tetramethylhex-5-en-3-one

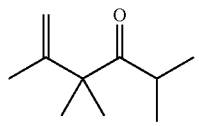

Potassium 2-methylpropan-2-olate (54.0 g, 481 mmol) was added to a solution of 4,4,5-trimethylhex-5-en-3-one (45.0 g, 321 mmol) in tetrahydrofuran (1.80 L) at 0° C. over a period of 40 min under nitrogen atmosphere. Then the mixture was stirred at 0-5° C. for 30 min. Subsequently, iodomethane (49.9 mL, 802 mmol) was added dropwise and then the mixture was stirred at 25° C. for 16 h. Saturated aqueous solution of ammonium chloride was added and the mixture was extracted with ethyl acetate (2×200 mL). Combined organic phases were dried over anhydrous $Na_2SO_4$ and volatiles removed under reduced pressure. Crude product (65.6 g) was purified by fractional distillation using ss-random packed column (0.3 m) to afford 2,4,4,5-tetramethylhex-5-en-3-one (36.2 g, 65.8%) as a colorless liquid.

$^1$H NMR (600 MHz, $CDCl_3$): δ 1.00 (d, J=6.7 Hz, 6H), 1.25 (s, 6H), 1.66 (s, 3H), 3.03-3.11 (m, 1H), 5.00 (brd, J=7.1 Hz, 1H).

$^{13}$C NMR (151 MHz, $CDCl_3$): δ 20.6, 20.8, 23.1, 34.0, 54.4, 112.3, 147.3, 218.2.

Step-2: Synthesis of 2,4,4,5-tetramethylhex-5-en-3-ol

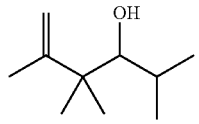

Sodium borohydride (14.72 g, 389 mmol) was added to a solution of 2,4,4,5-tetramethylhex-5-en-3-one (15.0 g, 97.0 mmol) in methanol (200 ml) at 0° C. over a period of 2 h. Then the mixture was stirred at 0° C. for 2 h and at 25° C. for 12 h. Subsequently, aqueous 5% hydrogen chloride solution was added at 0° C. till pH 7. The mixture was extracted with ethyl acetate (3×50 mL). The organic phases were combined and volatiles removed under reduced pressure (50° C./225 mbar). Crude product (15.3 g) was purified by silicagel chromatography using n-hexane/ethyl acetate (80/20) as eluent to afford 2,4,4,5-tetramethylhex-5-en-3-ol (12.2 g, 73.6%) as a colorless mixture.

$^1$H NMR (600 MHz, $CDCl_3$): δ 0.85 (d, J=6.8 Hz, 3H), 0.93 (d, J=6.8 Hz, 3H), 0.99 (s, 3H), 1.01 (s, 3H), 1.69 (s, 3H), 1.73-1.82 (m, 1H), 3.27 (d, J=3.2 Hz, 1H), 4.78 (s, 1H), 4.76-4.80 (m, 1H), $^{13}$C NMR (151 MHz, $CDCl_3$): δ 17.4, 19.7, 22.5, 23.6, 23.8, 28.8, 44.5, 79.6, 111.5, 151.6.

Example 10

Synthesis of 2,3,3-trimethylhept-1-en-4-ol

Step-1: Synthesis of 2,3,3-trimethylhept-1-en-4-one

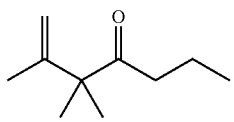

2,3-Dimethyl-2-butene (930 g, 11.0 mol) was added to a solution of zinc chloride (452 g, 3.31 mol) in butyric anhydride (1.75 kg, 11.0 mol) at 5° C. under nitrogen atmosphere while stirring. Then the mixture was warmed to 20° C. within 6 h and then stirred at 20° C. for 48 h. Subsequently, water was added (4.00 L). Separated organic phase was washed with water (1×4.00 L), aqueous saturated sodium carbonate solution till pH 7 and brine (1.00 L). The crude product (1.55 kg) was purified by distillation in vacuo (53-55° C./10 mbar) to afford 2,3,3-trimethylhept-1-en-4-one (1.24 kg, 60%) as a colorless liquid.

$^1$H NMR (400 MHz, $CDCl_3$): δ 0.80 (t, J=7.6 Hz, 3H), 1.15 (s, 6H), 1.43-1.52 (m, 2H), 1.55 (s, 3H), 2.31 (t, J=7.2 Hz, 2H), 4.88 (s, 2H).

$^{13}$C NMR (151 MHz, $CDCl_3$): δ 11.2, 14.9, 17.6, 20.2, 20.8, 35.8, 51.1, 109.1, 145.5, 211.1.

Step-2: Synthesis of 2,3,3-trimethylhept-1-en-4-ol

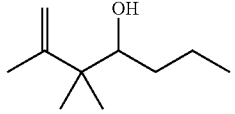

Sodium borohydride (590 mg, 16.0 mmol) was added to a solution of 2,3,3-trimethylhept-1-en-4-one (2.00 g, 13.0 mmol) in methanol (20.0 ml) for 20 min. Then, the mixture was stirred at 25° C. for 6 h. Subsequently, aqueous 5% solution of hydrogen chloride was added till pH 7. The mixture was extracted with ethyl acetate (3×50 mL) and the combined extracts were washed with water (50 mL). Volatiles were removed under reduced pressure to afford 2,3,3-trimethylhept-1-en-4-ol (1.92 g, 85%) as a colorless liquid.

$^1$H NMR (400 MHz, $CDCl_3$): δ 0.86 (t, J=7.2 Hz, 3H), 0.93 (s, 3H), 0.97 (s, 3H), 1.13-1.35 (m, 4H), 1.60 (bs, 1H), 1.67 (s, 3H), 3.38-3.41 (m, 1H), 4.77 (d, J=0.4 Hz, 1H), 4.82-4.83 (m, 1H).

$^{13}$C NMR (151 MHz, $CDCl_3$): δ 14.1, 19.8, 20.2, 21.5, 22.3, 33.2, 43.5, 75.0, 111.8, 151.1.

Example 11

Synthesis of (E)-2,3,3-trimethylhepta-1,5-dien-4-ol

Step-1: Synthesis of (E)-2,3,3-trimethylhepta-1,5-dien-4-one

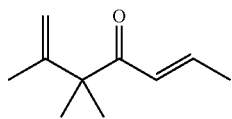

Zinc chloride (300 g, 2.20 mol) was added portion-wise to a solution of crotonic anhydride (1.26 kg, 8.15 mol) in methylcyclohexane (500 g) at −5° C. and the mixture was stirred for 20 min. Then 2,3-dimethylbut-2-ene (618 g, 7.34 mol) was added over a period of 4 h at −5° C. The mixture was stirred for 16 h at 25° C. Subsequently, water (1.50 L) was added. Separated organic phase was washed with aqueous 10% solution of sodium hydroxide (2.50 L), water (900 mL) and brine (600 mL) and volatiles were removed under reduced pressured. Crude product was purified by distillation in vacuo (38-43° C./2 mbar) to afford (E)-2,3,3-trimethylhepta-1,5-dien-4-one (469 g, 42%) as a colorless liquid.

$^1$H NMR (400 MHz, CDCl$_3$): δ 1.15 (s, 6H), 1.56-1.57 (m, 3H), 1.77 (dd, J=6.8, 1.6 Hz, 3H), 4.89-4.92 (m, 2H), 6.31 (dq, J=15.2, 1.6 Hz, 1H), 6.83-6.91 (m, 1H).

$^{13}$C NMR (151 MHz, CDCl$_3$): δ 17.8, 20.2, 23.02, 53.0, 111.9, 126.1, 142.1, 148.1, 203.9.

Step-2: Synthesis of (E)-2,3,3-trimethylhepta-1,5-dien-4-ol

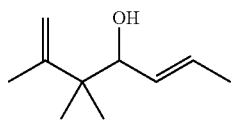

Cerium(III) chloride heptahydrate (2.47 g, 6.63 mmol) was added to a solution of (E)-2,3,3-trimethylhepta-1,5-dien-4-one (1.00 g, 6.57 mmol) in methanol (50.0 ml) at 25° C. The mixture was stirred at 25° C. for 30 min. Subsequently, sodium borohydride (249 mg, 6.57 mmol) was added at 0° C. and the mixture was stirred for at 0° C. for 2 h. Water (100 mL) was added and the mixture extracted with dichloromethane (3×50 mL). Combined organic extracts were dried over sodium sulphate and volatiles removed under reduced pressure. Crude product (967 mg) was purified by silica gel column chromatography using n-hexane/ethyl acetate mixture (80/20) as eluent to afford (E)-2,3,3-trimethylhepta-1,5-dien-4-ol (890 mg, 84%) as colorless liquid.

$^1$H NMR (400 MHz, CDCl$_3$): δ 0.89 (s, 3H), 0.98 (s, 3H), 1.64-1.67 (m, 4H), 1.70 (d, J=0.8 Hz, 3H), 3.85-3.87 (m, 1H), 4.80 (d, J=0.8 Hz, 1H), 4.87-4.88 (m, 1H), 5.37-5.44 (m, 1H), 5.59-5.67 (m, 1H).

$^{13}$C NMR (151 MHz, CDCl$_3$): δ 15.4, 17.8, 18.9, 21.4, 41.8, 75.1, 110.3, 126.7, 127.9, 148.8.

Example 12

Synthesis of 2,3,3,5-tetramethylhept-1-en-4-ol

Step-1: Synthesis of 2,3,3,5-tetramethylhept-1-en-4-one

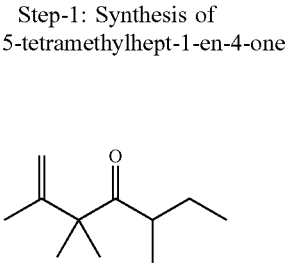

Potassium 2-methylpropan-2-olate (8.40 g, 74.9 mmol) was added to a solution of 4,4,5-trimethylhex-5-en-3-one (5.00 g, 35.7 mmol) in tetrahydrofuran (50.0 ml) under nitrogen atmosphere at 10° C. over a period of 15 min. Then, iodoethane (11.1 g, 71.3 mmol) was added dropwise and the mixture was allowed to warm up to 25° C. and stirred for 24 h. Subsequently, aqueous saturated ammonium chloride solution (50 mL) was added and the mixture extracted with methyl tert-butyl ether (2×50.0 mL). Combined organic extracts were dried over anhydrous sodium sulphate and volatiles removed under reduced pressure to afford 2,3,3,5-tetramethylhept-1-en-4-one (6.30 g, 90'%) as a colorless liquid.

$^1$H NMR (400 MHz, CDCl$_3$): δ 0.75 (t, J=7.6 Hz, 3H), 0.90 (d, J=6.8 Hz, 3H), 1.16 (s, 3H), 1.18 (s, 3H), 1.20-1.28 (m, 1H), 1.38-1.50 (m, 1H), 1.57 (s, 3H), 2.72-2.84 (m, 1H), 4.90 (s, 2H). $^{13}$C NMR (100 MHz, CDCl$_3$): δ 10.8, 17.2, 19.7, 22.3, 22.4, 26.5, 40.0, 53.4, 111.6, 146.2, 216.3.

Step-2: Synthesis of 2,3,3,5-tetramethylhept-1-en-4-ol:

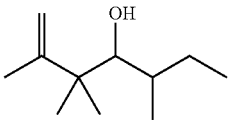

Sodium borohydride (340 mg, 8.91 mmol) was added slowly to a solution of 2,3,3,5-tetramethylhept-1-en-4-one (1.00 g, 5.94 mmol) in methanol (5.00 mL) was at 25° C. and the mixture was stirred at 25° C. for 20 h. Subsequently, aqueous 0.5 N solution of hydrogen chloride (10.0 mL) was added till pH 7 and the mixture was extracted with ethyl acetate (2×10 mL). Combined organic phases were washed with water (2×20 mL) and volatiles removed under reduced pressure to afford 2,3,3,5-tetramethylhept-1-en-4-ol (1.10 g, 86%) as a colorless liquid (mixture of diastereomers).

$^1$H NMR (400 MHz, CDCl$_3$): δ 0.75-0.85 (m, 6H), 0.96-1.01 (m, 6H), 1.21-1.35 (m, 1H), 1.40-1.56 (m, 3H), 1.69 (s, 3H), 3.30 (d, J=1.6 Hz, 0.5 H), 3.37 (d, J=1.6 Hz, 0.5H), 4.71 (s, 1H), 4.79-4.81 (m, 1H). $^{13}$C NMR (100 MHz, CDCl$_3$): δ 10.87, 13.01, 17.2, 22.0, 23.3, 33.8, 35.2, 43.4, 78.6, 110.5, 150.6.

Example 13

Alternative synthesis of (E)-2,3,3-trimethylhepta-1,5-dien-4-ol

Step-1: Alternative synthesis of (E)-2,3,3-trimethylhepta-1,5-dien-4-one

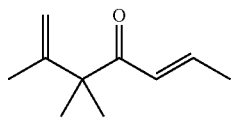

2,3-Dimethyl-1-butene (284 g, 405 mL, 3.38 mol) was added to a solution of trifluoromethanesulfonic acid (5.07 g, 3.0 mL, 33.8 mmol) in crotonic anhydride (521 g, 500 mL, 3.38 mol) at −20° C. under nitrogen atmosphere. Then the mixture was stirred at 0° C. for 30 min, and at 20° C. for 12 h. Subsequently, aqueous 2M sodium hydroxide solution (2.53 L, 5.07 mol) was added, the mixture was stirred at 50° C. for 4 hours under nitrogen atmosphere and cooled to 20° C. Then organic fraction was separated and the aqueous fraction was extracted with methyl tert-butyl ether (2.00 L). The combined organic fractions were washed with brine, and dried over sodium sulphate. The volatiles were removed under reduced pressure and the residue distilled in vacuo (50-52° C./4 mbar) to afford 2,3,3,6-trimethylhepta-1,5-dien-4-one (142 g, 22% yield).

Step-2: Synthesis of (E)-2,3,3-trimethylhepta-1,5-dien-4-ol: See example 11

The olfactory properties of a selection of the above compounds are given below:

| Compounds of formula (7-8) | Olfactory notes |
|---|---|
| 4,4,5-trimethylhex-5-en-3-ol | celery, pine needles. med, very diffusive, earthy but creamy, sweet/peppermint, slightly cooling. |
| 3,3,4-trimethylpent-4-en-2-ol | Medium-strong, camphor, slightly dirty, diffusive |
| 3,3,4-trimethylpentan-2-ol | medium, diffusive, piney, eucalyptol plus fatty, amyl alcohol direction |
| 2,3,3-trimethylhept-1-en-4-ol | fresh, floral, fruity, woody. |
| 2,4,4,5-tetramethylhex-5-en-3-ol | weak but woody, fruity, green |
| 2,3,3-trimethyloctan-4-ol | medium, diffusive, direction of isobornyl acetate but less earthy, piney |

Compositions Example

In the following invention example (A) and comparative examples (B/C/D), the compound of Example 1, and commercial compounds were included in a citrus accord fragrance for use in shampoo (E=blank). DPG=dipropylene glycol.

| Examples | A | B | C | D | E |
|---|---|---|---|---|---|
| Raw Materials (parts by weight) | | | | | |
| Aldehyde C10 | 40 | 40 | 40 | 40 | 40 |
| Citral | 25 | 25 | 25 | 25 | 25 |
| Citronellyl nitrile | 65 | 65 | 65 | 65 | 65 |
| Decalactone delta | 1 | 1 | 1 | 1 | 1 |
| Ethylmaltol | 2.5 | 2.5 | 2.5 | 2.5 | 2.5 |
| Hedione | 75 | 75 | 75 | 75 | 75 |
| Litsea Cubeba terpenes | 180 | 180 | 180 | 180 | 180 |
| Orange oil cold pressed | 560 | 560 | 560 | 560 | 560 |
| Trans-2-dodecenal | 2 | 2 | 2 | 2 | 2 |
| 4,4,5-Trimethylhex-5-en-3-ol 10% DPG | 10 | 0 | 0 | 0 | 0 |
| Borneol 10% DPG | 0 | 10 | 0 | 0 | 0 |
| Isobornyl acetate 10% DPG | 0 | 0 | 10 | 0 | 0 |
| Fenchyl acetate 10% DPG | 0 | 0 | 0 | 10 | 0 |
| Dipropylene glycol (DPG) | 39.5 | 39.5 | 39.5 | 39.5 | 49.5 |
| TOTAL | 1000 | 1000 | 1000 | 1000 | 1000 |

Comparative studies of different compounds where column E is the blank:

The introduction of 0.1% by weight of 4,4,5-trimethylhex-5-en-3-ol enhances the citrus effect giving the fragrance a more sparkling and more natural and fresher character (A).

Compared to this material the following effects are observed with reference materials:

The introduction of 0.1% by weight of borneol provides this citrus accord with a more piney, albeit noticeably synthetic effect (B).

The introduction of 0.1% by weight of isobornyl acetate gives no noticeable effect to this citrus accord (C).

The introduction of 0.1% by weight of fenchyl acetate provides this citrus accord with a more piney and slightly minty effect but without the natural and fresh character of composition A (D).

The invention claimed is:
1. Fragrance, flavor and/or deodorizing/masking compositions comprising an alcohol selected from compounds of formula (7) or of formula (8)

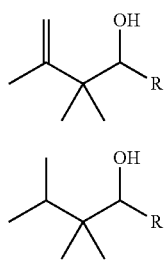

(7)

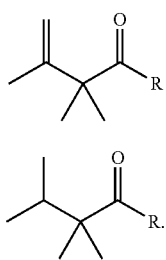

(8)

wherein R is an alkyl group having from 1 to 6 carbon atoms, or an alkenyl group having from 2 to 6 carbon atoms, and wherein compound of formula (8) can't be 2,3,3,5,5,6-hexamethylheptan-4-ol; and at least one of its parent ketone of formula (5) or of formula (6)

(5)

(6)

2. Fragrance, flavor and/or deodorizing/masking compositions according to claim 1 wherein R is methyl, ethyl, n-propyl, i-propyl, n-butyl, s-butyl, t-butyl, i-butyl, 2-methylprop-1-en-2-yl, n-pentyl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

3. Fragrance, flavor and/or deodorizing/masking compositions according to claim 2 wherein for the compounds of formula (7) R can't be methyl, i-propyl, or i-butyl, and the compound of formula (7) can't be 2,3,3,5,5,6-hexamethylhepta-1,6-dien-4-ol or 2,3,3,6,7-pentamethylocta-1,6-dien-4-ol, and for the compounds of formula (8) R can't be vinyl.

4. Fragrance, flavor and/or deodorizing/masking compositions according to claim 1 wherein the alcohol is selected from any of the compounds named or drawn in the following table

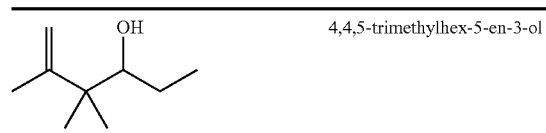

4,4,5-trimethylhex-5-en-3-ol 4,4,5-trimethylhexan-3-ol 3,3,4-trimethylpent-4-en-2-ol 3,3,4-trimethylpentan-2-ol 2,3,3-trimethylhept-1-en-4-ol 2,3,3-trimethylhepta-1,5-dien-4-ol 2,4,4,5-tetramethylhex-5-en-3-ol 2,3,3-trimethyloct-1-en-4-ol 2,3,3-trimethyloctan-4-ol 2,3,3-tetramethylnon-1-en-4-ol 2,3,3-trimethylnonan-4-ol 2,3,3,5-tetramethylhept-1-en-4-ol and/or a mixture of two or more of the said alcohols.

5. Fragrance, flavor and/or deodorizing/masking compositions according to claim 1 wherein the content of the compounds of formula (7) and/or of formula (8) is comprised between 0.00001 and 99.9 wt. %.

6. Fragrance, flavor and/or deodorizing/masking compositions according to claim 1 additionally comprising at least one ester and/or one other alcohol.

7. Fragrance, flavor and/or deodorizing/masking compositions according to claim 6 wherein the total content of the compound(s) of formula (7) and/or of formula (8) together with the ester(s) and/or other alcohol(s) is superior to 25 wt %.

8. Fragrance, flavor and/or deodorizing/masking compositions according to claim 1 comprising a mixture of at least one alcohol of formula (7) and one alcohol of formula (8).

9. Fragrance, flavor and/or deodorizing/masking compositions according to claim 1, wherein the weight ratio between the parent ketone and its alcohol is comprised between 0.001 and 0.2.

10. Fragrance, flavor and/or deodorizing/masking compositions comprising an alcohol, wherein the alcohol is selected from compounds of formula (7) or of formula (8)

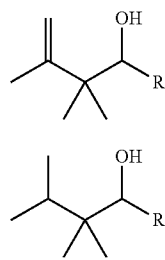

wherein R is an alkyl group having from 1 to 6 carbon atoms, or an alkenyl group having from 2 to 6 carbon atoms, and wherein compound of formula (8) can't be 2,3,3,5,5,6-hexamethylheptan-4-ol; and wherein for the compounds of formula (7) R is an alkyl group having from 2 to 6 carbon atoms, or an alkenyl group having from 2 to 6 carbons, with the proviso that R can't be i-propyl, or i-butyl, and compound of formula (7) can't be 2,3,3,5,5,6-hexamethylhepta-1,6-dien-4-ol or 2,3,3,6,7-pentamethylocta-1,6-dien-4-ol, and wherein for the compounds of formula (8) R is an alkyl group having from 2 to 6 carbon atoms, or an alkenyl group having from 3 to 6 carbons, with the proviso that R can't be i-propyl, and compound of formula (8) can't be 2,3,3,5,5,6-hexamethylheptan-4-ol.

11. Alcohol useful in a fragrance, flavor and/or deodorizing/masking composition according to claim 10 wherein the alcohol is selected from compounds of formula (7) or of formula (8)

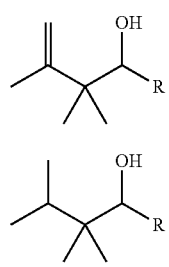

wherein for the compounds of formula (7), R is ethyl, n-propyl, n-butyl, s-butyl, t-butyl, n-pentyl, 2-methylprop-1-en-2-yl, 2-pentyl, 3-pentyl, n-hexyl, 2-hexyl, 3-hexyl, vinyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl, and for the compounds of formula (8), R is ethyl, n-propyl, n-butyl, s-butyl, t-butyl, i-butyl, n-pentyl, 2-pentyl, 3-pentyl, n-hexyl, 2-hexyl, 3-hexyl, 1-propenyl, prop-1-en-2-yl, allyl, 1-butenyl, 2-butenyl, but-3-en-2-yl, 1-pentenyl, pent-2-en-1-yl, pent-3-en-1-yl, pent-4-en-1-yl, pent-1-en-2-yl, 2-pentenyl, pent-3-en-2-yl, pent-4-en-2-yl, pent-2-en-3-yl, pent-1-en-3-yl, 1-hexenyl, hex-2-en-1-yl, hex-3-en-1-yl, hex-4-en-1-yl, hex-5-en-1-yl, hex-1-en-2-yl, 2-hexenyl, hex-3-en-2-yl, hex-4-en-2-yl, hex-5-en-2-yl, 3-hexenyl, hex-1-en-3-yl, hex-2-en-3-yl, hex-3-en-3-yl, hex-4-en-3-yl, or hex-5-en-3-yl.

12. Alcohol according to claim 11 wherein for the compounds of formula (7), R is ethyl, n-propyl, n-butyl, n-pentyl, n-hexyl, vinyl, 1-propenyl, 1-butenyl, 1-pentenyl, or 1-hexenyl, and for the compounds of formula (8), R is ethyl, n-propyl, n-butyl, n-pentyl, n-hexyl, 1-propenyl, 1-butenyl, 1-pentenyl, or 1-hexenyl.

13. Fragrance, flavor and/or deodorizing/masking compositions comprising an alcohol selected from compounds of formula (7) or of formula (8)

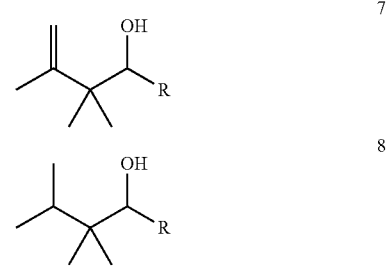

wherein R is an alkyl group having from 1 to 6 carbon atoms, or an alkenyl group having from 2 to 6 carbon atoms, and wherein compound of formula (8) can't be 2.3.3.5.5.6-hexamethylheptan-4-ol; and wherein the alcohol is selected from any of the compounds named or drawn in the following table

| | |
|---|---|
| (structure) | 4,4,5-trimethylhex-5-en-3-ol |
| (structure) | 4,4,5-trimethylhexan-3-ol |

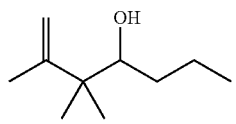 2,3,3,-trimethylhept-1-en-4-ol

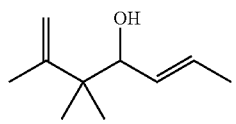 (E)-2,3,3-trimethylhepta-1,5-dien-4-ol

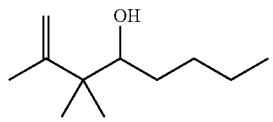 2,3,3-trimethyloct-1-en-4-ol

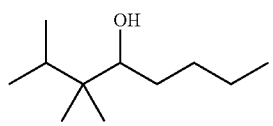 2,3,3-trimethyloctan-4-ol

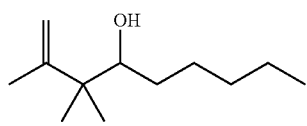 2,3,3-trimethylnon-1-en-4-ol

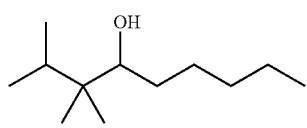 2,3,3-trimethylnonan-4-ol

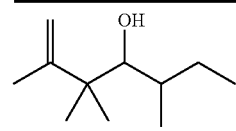 2,3,3,5-tetramethylhept-1-en-4-ol.

14. Fragrance, flavor and/or deodorizing/masking compositions according to claim 1 wherein the content of the compounds of formula (7) and/or of formula (8) is comprised between 0.00001 and 95 wt %.

15. Fragrance, flavor and/or deodorizing/masking compositions according to claim 1 additionally comprising a mixture of ester and other alcohol.

16. Fragrance, flavor and/or deodorizing/masking compositions according to claim 6 wherein the total content of the compound(s) of formula (7) and/or of formula (8) together with the ester(s) and/or other alcohol(s) is superior to 50 wt %.

17. Fragrance, flavor and/or deodorizing/masking compositions according to claim 6 wherein the total content of the compound(s) of formula (7) and/or of formula (8) together with the ester(s) and/or other alcohol(s) is superior to 75 wt %.

18. Fragrance, flavor and/or deodorizing/masking compositions according to claim 6 wherein the total content of the compound(s) of formula (7) and/or of formula (8) together with the ester(s) and/or other alcohol(s) is superior to 90 wt %.

19. A method of applying a fragrance, flavor and/or deodorizing/masking composition according to claim 1 to a perfumed or flavored product.

20. A method of applying an alcohol according to claim 10 to a perfumed or flavored product.

* * * * *